United States Patent [19]

Kemlo

[11] Patent Number: 4,818,936
[45] Date of Patent: Apr. 4, 1989

[54] METHOD AND APPARATUS FOR IDENTIFYING AND CLASSIFYING STEELS

[75] Inventor: Kenneth G. Kemlo, Lambton, Australia

[73] Assignee: The Broken Hill Proprietary Company Limited, Victoria, Australia

[21] Appl. No.: 932,509

[22] PCT Filed: Feb. 17, 1986

[86] PCT No.: PCT/AU86/00039
§ 371 Date: Oct. 14, 1986
§ 102(e) Date: Oct. 14, 1986

[87] PCT Pub. No.: WO86/04991
PCT Pub. Date: Aug. 28, 1986

[30] Foreign Application Priority Data

Feb. 15, 1985 [AU] Australia .............................. PG9314

[51] Int. Cl.⁴ ...................... G01N 27/72; G01R 33/12
[52] U.S. Cl. ...................................... 324/232; 324/233
[58] Field of Search ............... 324/227, 228, 232, 233, 324/239, 243, 234, 225

[56] References Cited

U.S. PATENT DOCUMENTS

| | | |
|---|---|---|
| 2,331,418 | 10/1943 | Nolde . |
| 3,434,048 | 3/1959 | Law . |
| 3,686,564 | 8/1972 | Mallick, Jr. et al. .............. 324/232 |
| 3,825,820 | 7/1974 | Flaherty et al. .................... 324/227 |
| 4,006,405 | 2/1977 | Greenwood et al. .............. 324/227 |
| 4,075,553 | 2/1978 | Bouverot et al. .................. 324/233 |
| 4,086,527 | 4/1978 | Cadot .................................. 324/233 |
| 4,237,419 | 12/1980 | Tönblom et al. ............... 324/232 X |
| 4,263,551 | 4/1981 | Gregory et al. .................... 324/233 |
| 4,475,083 | 10/1984 | Linder . |
| 4,493,039 | 1/1985 | Gregory ........................ 324/233 X |
| 4,563,644 | 1/1986 | Lenander et al. .................. 324/232 |
| 4,661,777 | 4/1987 | Törnblom ..................... 324/232 X |

FOREIGN PATENT DOCUMENTS

| | | |
|---|---|---|
| 46546 | 4/1979 | Australia . |
| 71756 | 5/1981 | Australia . |
| 0049951 | 10/1981 | European Pat. Off. . |
| 58-45548 | 3/1983 | Japan .................................. 324/232 |
| 17350 | 7/1983 | Japan . |
| 1095058 | 3/1982 | U.S.S.R. . |

OTHER PUBLICATIONS

Tso, "Tower Concentration Meter", Xerox Disclosure Journal, vol. 5, No. 3, May/Jun. 1980, p. 315.

Primary Examiner—Reinhard J. Eisenzopf
Assistant Examiner—Warren S. Edmonds
Attorney, Agent, or Firm—Armstrong, Nikaido, Marmelstein & Kubovcik

[57] ABSTRACT

Method and apparatus for identifying and classifying steels in which a steel specimen is presented to a coil which receives an excitation current to produce an electrical output dependent on an induction value of the specimen. An excitation current is applied to the coil at each of a plurality of excitation frequencies, and a respective value of the specimen at each of those frequencies is determined. The value of a discriminant function is derived for each of a plurality of possible steel grades, with the function being of the form $a\alpha + b\beta + c\gamma \ldots$ where $\alpha, \beta, \gamma \ldots$ are attributes of the specimen comprising the induction values and a, b, c ... are predetermined coefficients reflecting the degree to which the respective attributes are effective to discriminate that possible steel grade from the others. The possible grade which correlates with a maximum discriminant function value is determined in order to achieve the desired identification and classification of the steel specimen.

10 Claims, 9 Drawing Sheets

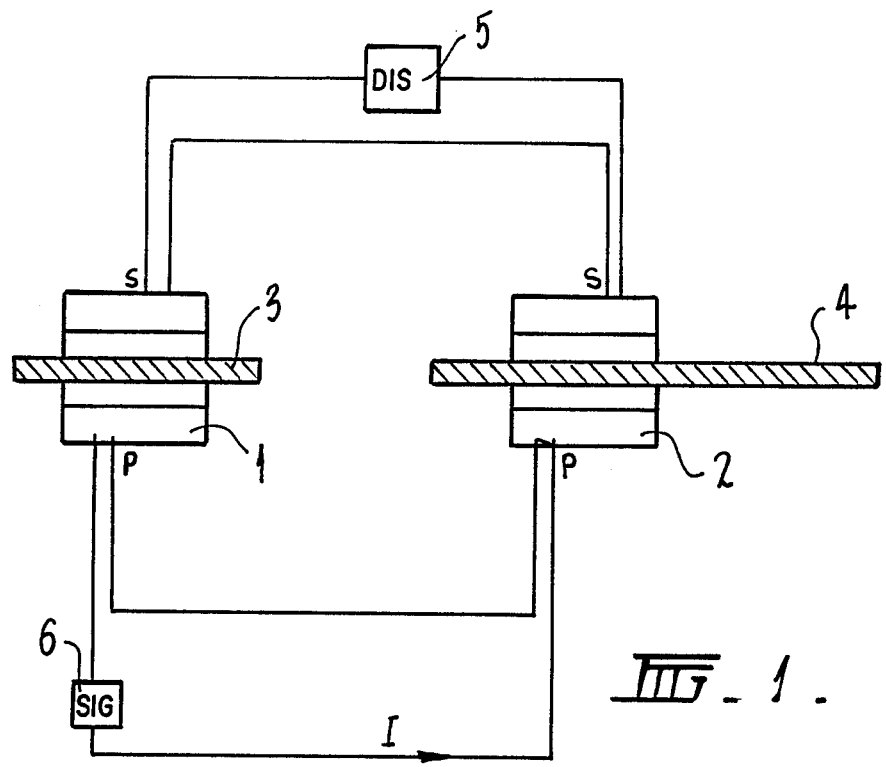
FIG_1.
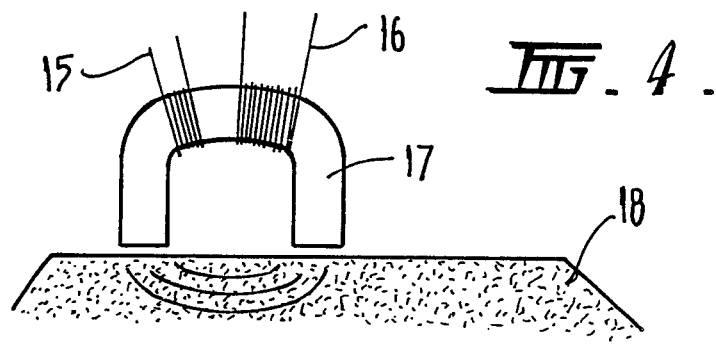
FIG_4.

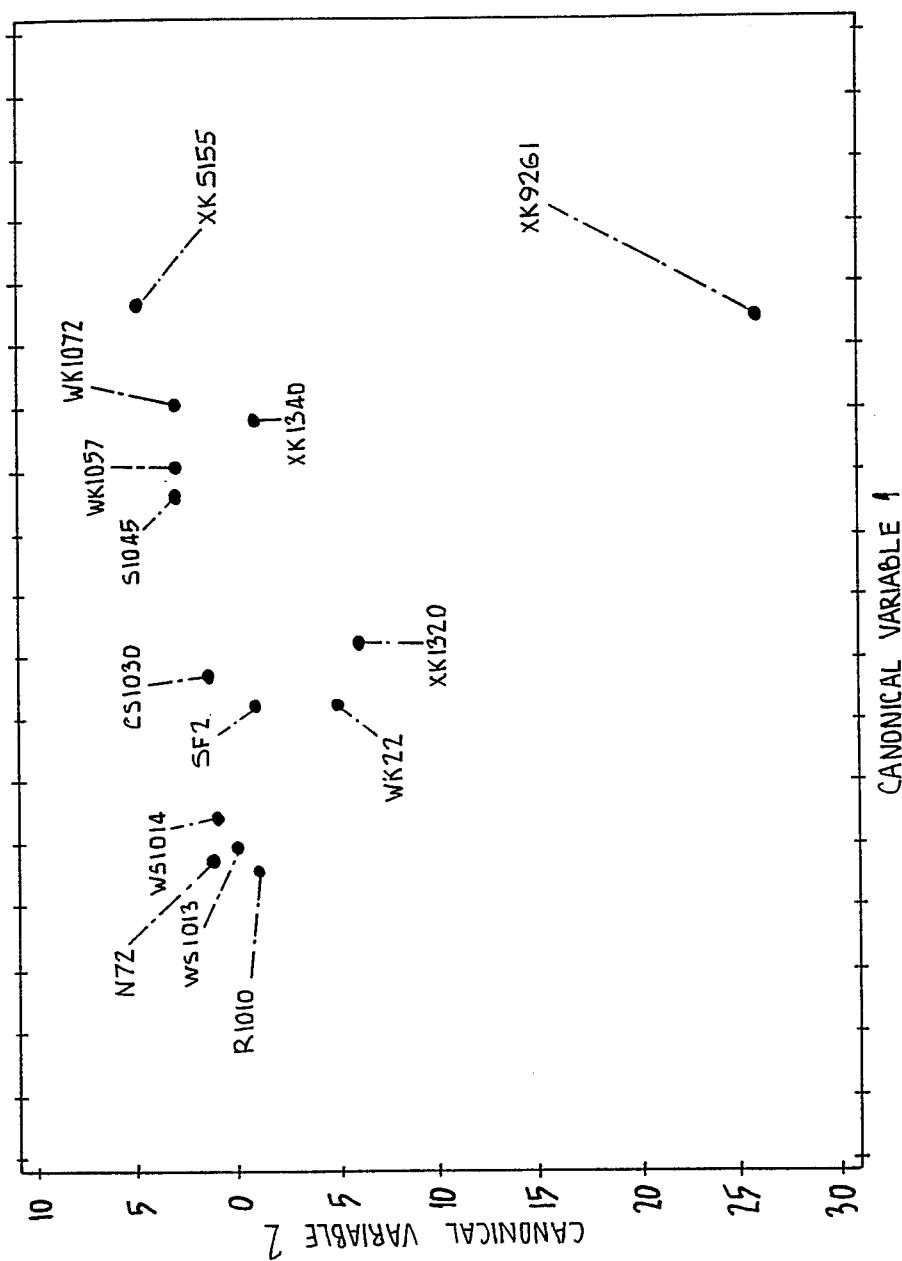
FIG_5.

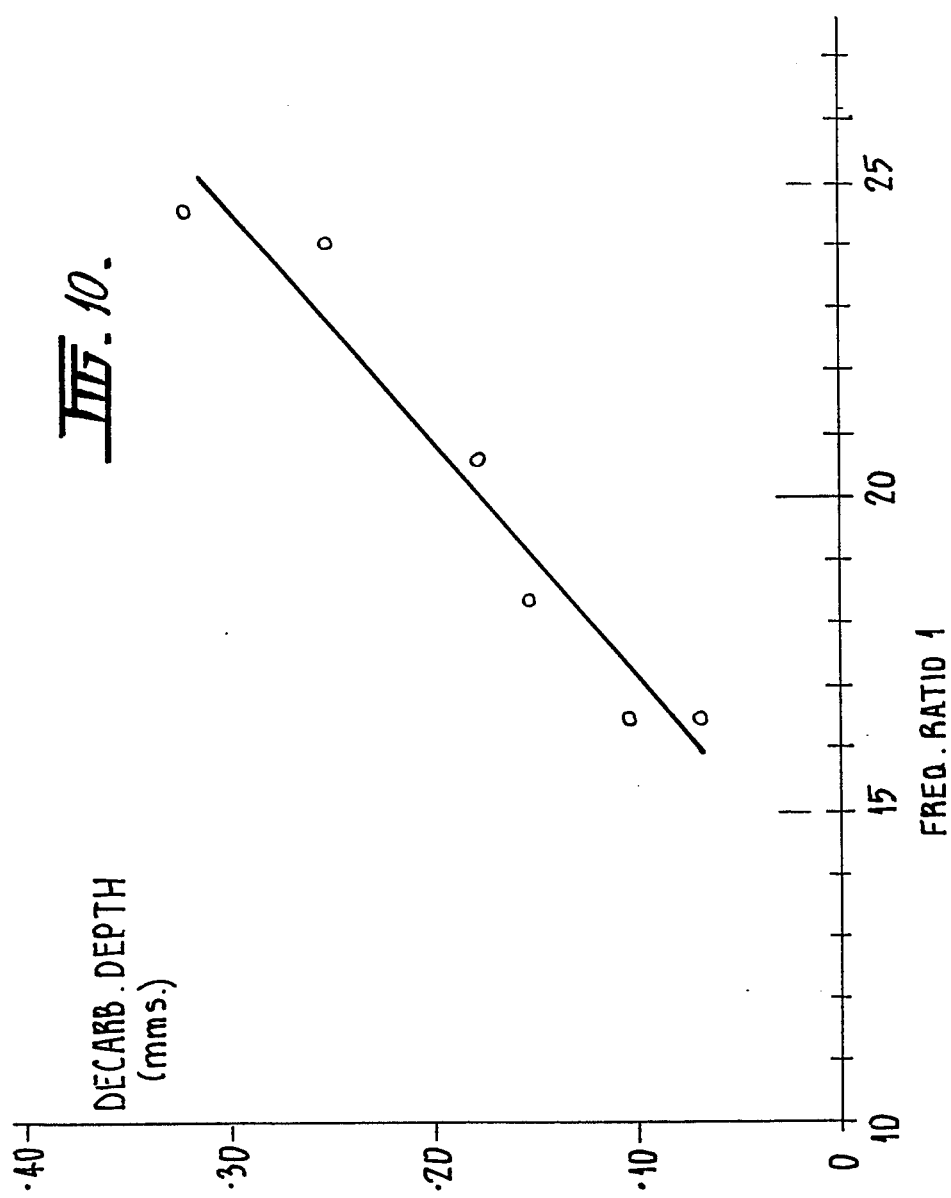

METHOD AND APPARATUS FOR IDENTIFYING AND CLASSIFYING STEELS

TECHNICAL FIELD

This invention relates to methods and apparatus for identifying and classifying steels.

BACKGROUND ART

In a modern steel works producing a wide range of steel products of differing steel grades, it is important to be able to carry out non-destructive testing of steel specimens to establish their correct grades. One current method, known as the "Forster" method, relies on a comparison between the magnetic properties of a steel specimen to be tested and a "standard" sample which has been chemically analysed. The test specimen and the standard sample are inserted into separate coils, each having primary and secondary windings. The primary windings of the two coils are subjected to a common energizing current of fixed frequency and a comparison is made between output signals induced in the secondary windings of the two coils. The output signals may be applied to a comparison circuit which generates a display on a screen.

The Forster method of steel classification has several limitations and problems in practice. These include:

1. A highly trained operator is required to interpret the trace or screen display to enable satisfactory information to be gained.

2. Since the operator must visually access a visual display, estimating the amplitude and shape of a wave form generated by the test sample, only a qualitative idea is obtined of possible differences between successive samples being tested.

3. Since the test method is not quantitative and since there are always some variations in the physical and chemical properties even within a given grade of steel, it is very difficult to be certain whether an observed changed in the display constitutes a real change in grade or only a variation explainable by within grade variations.

4. The method is very sensitive in variations in temperature between the test specimen and the standard sample.

5. Results depend on chemical analysis of the initial standard sample. Once it is considered that a change in grade has occurred the new grade cannot be determined without further recourse to sampling and subsequent chemical analysis.

The present invention has arisen from work aimed at developing an improved magnetic testing method which will enable a more accurate and convenient testing procedure.

DISCLOSURE OF INVENTION

The invention provides a method of classifying a steel specimen comprising:

presenting the specimen to a coil means having a primary winding and a secondary winding such that the specimen contributes to an inductive coupling between the primary winding and the secondary winding;

applying an excitation current to the primary winding at each of a plurality of excitation frequencies whereby to induce in the secondary winding for each excitation frequency a signal indicative of an induction value of the specimen; and determining a grade classification of the specimen dependent on the induction values obtained at said excitation frequencies.

The primary and secondary windings of the coil means may be generally co-axial and spaced apart in the axial direction and the specimen may be positioned so as to extend into both windings.

Alternatively, the primary and secondary windings may be disposed about a coupling member defining a coupling gap and the specimen may be position so as to provide an inductive coupling across said gap.

Preferably, the critical frequencies at which signals induced in the secondary winding are exactly out of phase with the excitation current are also determined and the determination of the grade classification is also dependent on those critical frequencies.

Preferably further, the grade classification is determined according to the value of a discriminant function of the form $a\alpha + \beta b + c\gamma + \ldots$ where $\alpha, \beta, \gamma \ldots$ are attributes of the specimen comprising said induction values and a, b, c ... are coefficient reflecting the degree to which the respective attributes are effective to discriminate between steel grades.

Preferably said attributes also comprise said critical frequencies.

The invention also provides apparatus for classifying steel specimens, comprising:

coil means having a primary winding and a secondary winding to be inductively coupled via a steel specimen to be classified;

excitation means for applying an excitation current to the primary winding at each of a plurality of excitation frequencies whereby to induce in the secondary winding for each frequency an output signal indicative of an inductive value of the specimen; and signal processing means to receive the output signals indicative of the induction values at said frequencies and to determine a grade classification of the specimen dependent on those values.

BRIEF DESCRIPTION OF THE DRAWINGS

In order that the invention may be more fully explained, the operation of one particular form of equipment, and the results obtained, will be described in detail with reference to the accompanying drawings in which:

FIG. 1 is a circuit diagram of conventional equipment operating on the "Forster" method;

FIGS. 2, 3 and 4 illustrate equipment operable in accordance with the present invention;

FIG. 5 is a canonical variable plot for various steel grades;

FIG. 10 is a graph showing a correlation between the decarburisation depth and measured inductions at various frequencies.

MODE FOR CARRYING OUT THE INVENTION

Figure 2:
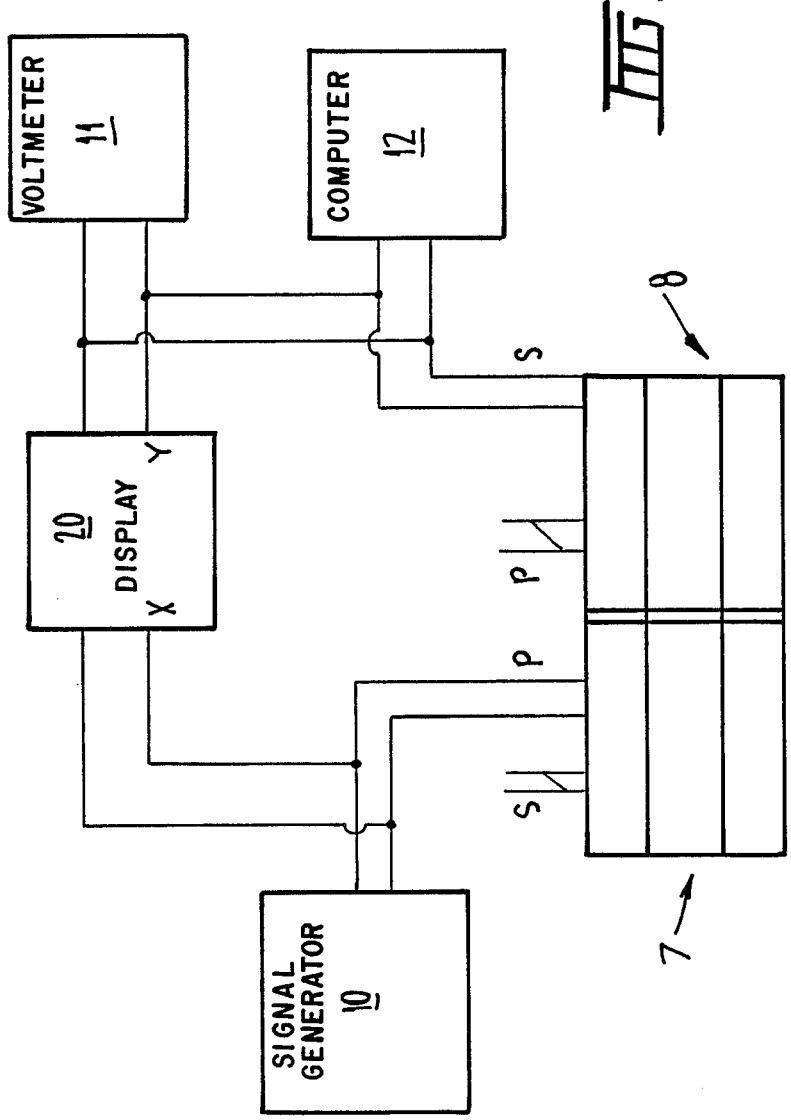

Apparatus conventionally used for classifying specimens by the "Forster" method is shown in FIG. 1. Two independent coils 1, 2 are used and comparisons are made between a chemically analysed sample 3 inserted into coil 1 and the test sample 4 inserted into coil 2. The primary windings of the coils are connected to 50 hz signal source 6 so that the same current (I) flows through the primaries (P) of both coils and a comparison is made between the two secondaries (S).

If the samples are the same, a balanced condition is effectively contained between S1 and S2. A change in magnetic properties of the test sample causes an imbalance in the electrical circuit, resulting in a change to the visual display pattern on the screen of the cathode ray tube instrument 5.

Figure 3:
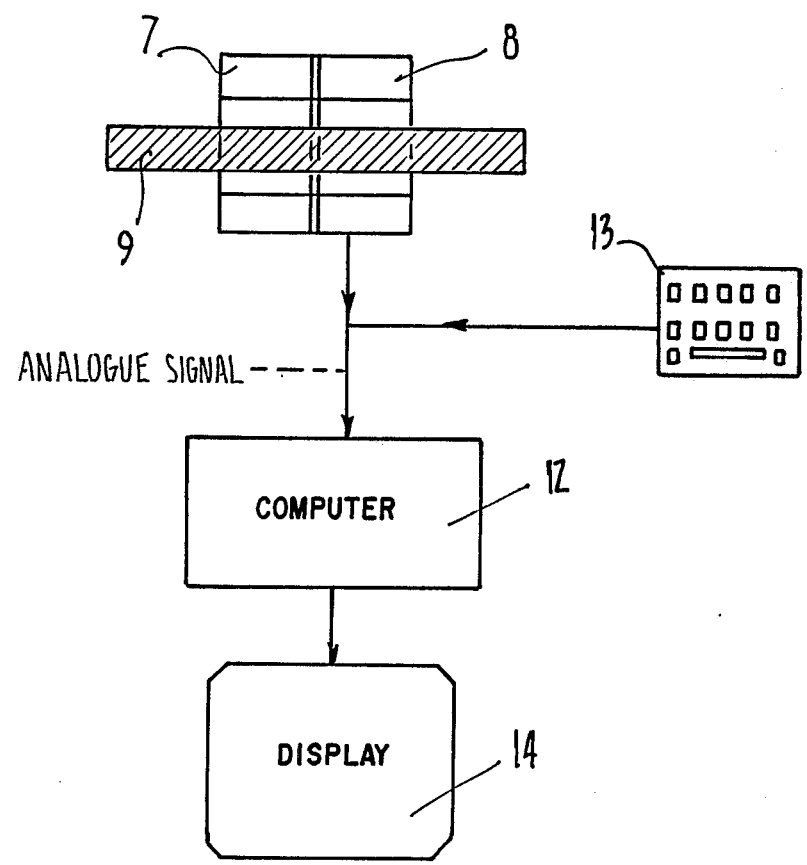

One apparatus for testing in accordance with the present invention is illustrated in FIGS. 2 and 3. In this apparatus two coils 7, 8 are strapped together with their axes aligned, to enable a steel specimen 9 to be inserted through both coils.

An excitation current delivered from a signal generator 10 is applied to the ends of the primary winding of the first coil 7 and the induced EMF is measured in a high impedance load (10M.ohms) connected to the secondary winding of the second coil 8. The secondary winding of the first coil (S1) and the primary winding of the second coil (P2) are not used.

It is possible to use one coil only by using the primary as driver and secondary as receiver, but the induced voltages from the primary which occur even without a sample threading the coil is sufficient to reduce the sensitivity to a large extent.

The output (secondary) from coil 8 is measured on a digital voltmeter 11 in parallel with a coaxial connection to a mini-computer 12. The input and output signals are displayed on a cathode ray oscilliscope 20. The computer, a MINC-11 (DEC) has an input keyboard 13, performs an analog to digital conversion on the as received signal and displays an output on a V.D.U. display screen 14.

Instead of using two coils each with primary and secondary windings, it would be possible to employ a single coil with primary and secondary windings spaced apart in the axial direction and arranged so that the steel specimens can be inserted through both.

FIG. 4 illustrates an alternative coil arrangement for dealing with specimens which are too large to be accommodated within the confines of a coil. In this arrangement primary and secondary coil windings 15, 16 are dispersed on a horseshoe-shaped coupling member 17, the ends of which define a coupling gap which, in use of the apparatus, bridged by a steel test specimen 18 so that the specimen contribute to the inductive coupling between the primary and the secondary windings.

The method of classifying steel specimens according to their grade type in accordance with the invention is based on a statistical procedure known as Linear Discriminant Analysis. Computer software packages that perform this statistical technique are available for a range of computer operating systems. One particular program suitable for this purpose is program P7M of the BMDP package (Bio Medical Statistical Programs issued by the Regents of the University of California) running on a PDP 11/70 computer using the RSX-11M operating system.

This program determines the minimum number of variables which will achieve the optimum statistical separation of the known steel grades types.

Data from a large number of steel specimens of various grade types are collectively called a "learning set".

Each specimen (or case) in the learning set has been processed using the coil arrangement to obtain quantitative induction data at various frequencies. These calculated variables as well as grade code (a convenient numerical identifier corresponding to the alpha-numeric grade name), are used as input to the P7M program.

All steel spcimens of a particular grade code are grouped together by the program. Variables that show merit in separating grade couplings on a quantitative statistical basis then become part of the linear discriminant equation. At each step, one variable will enter to be removed from the current list of optimum variables.

The linear discriminant function that uses the chosen variables will differ between grade codes by the coefficient and constant terms applied. That is, each grade will have an equation, comprised of differing coefficients applied to the same chosen variables.

For any specimen the numerical value of its known variables may be substituted into the equation for each grade code, to generate a numerical result. The particular equation that achieves the highest numerical result is deemed, on a statistical basis, to show which of the grade types known to the program most closely resembles the specimen in question.

In order to test the reliability of the procedure, the discriminant equations can be used to classify each of the steel specimens that form the learning set. The calculated grade may be compared with the known grade to report the percentage of agreements.

To test specimens on-line, or in the field, the values of the variables, viz. the inductions of various frequencies, are obtained, and fed into those same discriminant equations that were calculated off line. However, in the on-line case, the grade is unknown, and so the grade name whose equation gives the highest result, is classed on the grade of the unknown specimen.

In a series of classification tests on steel specimens a sampling time of two seconds (2 secs) was used in order to capture the signal induced by each specimen and the RMS signal strength was calculated for each current frequency applied to the input primary coil (from the signal generator).

A series of applied current frequencies were used viz; 5, 10, 50, 500, 5000, 10000 hertz.

In addition to these direct inputs to the MINC-11 via the A to D interface, additional information was supplied via the keyboard. This information consisted of:
 (i) The section (diameter of steel specimen)
 (ii) The natural frequency (in hertz)
 (iii) The coil frequency (in hertz)

The natural and coil frequency values were measured by connecting the input (driving) current to the X channel of a cathode ray oscilloscope (CRO) and the output signal to the Y channel.

If the frequency of the exciting current is slowly increased from zero (by rotating the frequency control potentiometer of the signal generator), the relative phase relationship between the two can be monitored. At a limited number of critical frequencies (determined by the coil design) the input and output signals are exactly out of phase (180°). The introduction of a steel specimen into the coils changes the frequency at which this out of phase condition occurs. The lower frequency measured is called the "natural" frequency and the higher frequency, the "coil" frequency.

These two values were entered manually to the MINC-11. However, with more sophisticated equipment this information may be automatically measured by a sweep frequency technique when the sample is first presented to the coil.

The computer presents the actual RMS inductions in the secondary at the frequency values used to excite the primary coil and the ACTUAL CODE it has determined the sample to be.

The samples used were all obtained from the laboratory sampling room in the as-rolled condition.

All specimens were rounds or rods and in the range 5.5 mm–20 mm the upper limit being dictated by the coil size.

The samples were examined and tested in the as received condition (usually slightly convex in shape with some minor scale present on the surface).

The resistance of the primary coil was not matched to that of the signal generator output resistance and consequently the available current into the primary coil varied to a large degree depending on the frequency of the applied current.

In order to ensure that the measurements obtained resulted from the effects of inserting the sample, and not from the induction between the coils, the induced EMF when no sample was present was measured for the frequencies of interest.

These values were referred to as the background values and were subtracted from the appropriate induction values obtained during the testing of the samples.

| I | = | T | − | B |
|---|---|---|---|---|
| Induction at 50 hz due to sample (Relative) | = | Total Induction at 50 hz measured (Absolute) (Sample inserted) | − | Background (at 50 hz) Induction (No sample) |

Table 1 of the Appendix shows a computer summary sheet for a portion of the information collected during this investigation. Column 1 of this table indicates the as received sample identification number, 2 the section diameter which is entered via the computer keyboard and columns 3 to 8 refer to the induction (I) at the frequencies indicated. The natural frequency (in hertz) is shown in column 9 and the coil frequency in 10. Column 11 is the actual grade of steel of the specimen.

Tables 2 and 3 show the chemical analysis, the inductions and the computed grade classification for a few of the samples tested.

The program which collects the voltage waveform from the output coil is also responsible for managing the data which is used for recording new sample information and also for testing specimens on-line. The data file from this program was transferred to a main processing computer, for analysis by the DMDP discriminant analysis program (P7M). This program is effective to choose which of the pieces of information collecting during testing, known as "attributes", will be most useful in describing the differences between individual specimens classified into their actual grades. For example, the measured induction values at 5,000 hertz may not discriminate well between two particular grade codes whereas the program may find significant differences between the induction values at 5 hertz. It therefore uses the $I_5$ value in preference to the $I_{5000}$ value to separate these two grades.

In reality (with 8 attributes and hundreds of samples) the simple two-dimensional separation mentioned above translates into 8th dimensional space.

The program uses a weighting procedure to emphasize the extent to which each attribute will be used to get the maximum separation that is possible (i.e. the best discrimination one grade from another) from the supplied data.

The output of the programme results from the following types of equation.

A variable $X = a\alpha + b\beta + c\gamma + \ldots$

Where $\alpha$, $\beta$, $\gamma$ are attributes and a,b,c are constants determined from the statistical analysis.

e.g. $X = 23 \times (I_{50}) + 49(I_{5000}) + 526(I_5) + \ldots$ 8 terms

In the case above it has calculated that $I_5$ is very important to the discriminant procedure with $I_{5000}$ less so (49 526) and $I_{50}$ even less so (23 49 526).

A look up table of X values then will yield the grade.

e.g. after a learning set has been input to the computer.

| Value Range X | Grade |
|---|---|
| 5–90 | WK1082 |
| 91–200 | WK1072 |
| 201–400 | WK1057 etc. |

If X is in range specified print out grade code.

e.g. X calculated = 300 PRINT "GRADE IS WK1057"

a, b, c once calculated on a reasonable large machine can be entered into a smaller (e.g. MINC-11 machine) ready for the testing of new samples.

| e.g. Result of main P7M run |
|---|
| a = 15.2 |
| b = 9.7 |
| c = 23.5 |
| d = −5.2 |
| e = 7.5 |
| f = 5.1 |
| g = 29.6 |
| h = 393.1 |

Placing a NEW sample to be identified into the coil—the small computer sets up the equation to be solved as follows:

$X = 15.2 \ (I_5) + 9.7 \ (I_{10}) + 23.5 \ (I_{50}) - 5.2 \ (I_{500}) + 7.5 \ (I_{5000}) +$ $5.1 \ (I_{10000}) - 29.6 \ (\text{Natural freq. value}) +$ $393.1 \ (\text{Coil. freq. value})$ ready for the sample to be processed
when the sample is processed and the inductions and frequency values determined the simple linear equation is solved.

e.g. $I_5 = 2.3$
$I_{10} = 3.5$
$I_{50} = 5.0$
$I_{500} = 6.5$
$I_{5000} = 23.5$
$I_{10000} = 30.2$
Nf = 50

-continued

Cf = 30000

Then X=15.2×2.3+9.7×3.5+23.5×5.0+ ... etc. X table is searched for the value of X calculated and the grade outputted.

The data from the classification tests was grouped together by using a grade code variable to be the independent variable. Some initial restructuring of the data was necessary for two reasons:

(i) Although 50 grade codes were available from the sample, many were represented by only one or two cases.

Some grades are closely similar and were grouped together (e.g. the silicon grades WK22 and R207). Such grades were classified as one code or "generic" name.

(ii) A reduction the number of codes available (generic names) was made necessary because of limitations to the available memory which restricted the total number of cases available for analysis. This upper limit was dependent on the number of groups (grade codes), and variables which were chosen for inclusion in the program's control language.

The program P7M, performs stepwise so that, for each step, the variable which allows the best discrimination (grade separation) is entered. Each equation, one for each grade is a linear function of the chosen variables.

For each specimen tested the most probable grade was determined by the linear discriminant function which has the maximum value. The probability that the specimen is each of the grade codes represented was calculated from the discriminant equations.

The BMDP result file, containing the classification function coefficients was transferred, via floppy diskette, to the MINC-11.

The output grade is one of the "generic" grades inputted to the program. For example a sample whose actual grade specification is AS 1302, would be classified to the generic code of SF2 (see FIG. 4c, Case No. 36).

The BMDP statistical package outputs its results in the form of a classification matrix. This tabulated information is read as follows:

EXAMPLE 1

Assume that 50 samples are to be classified into five categories or grades (Categories A, B, C, D and E).

If classification is perfect, the following computer result would be obtained:

|  |  |  | Computer Result | | | | |
| --- | --- | --- | --- | --- | --- | --- | --- |
|  |  |  | A | B | C | D | E |
| Actual | A | 100% | 7 |  | 0 | 0 | 0 |
| Grade | B | 100% | 0 | 10 | 0 | 0 | 0 |
|  | C | 100% | 0 | 0 | 12 | 0 | 0 |
|  | D | 100% | 0 | 0 | 0 | 13 | 0 |
|  | E | 100% | 0 | 0 | 0 | 0 | 8 |
|  |  | 100% |  |  |  |  |  |

The actual grade of the specimen (as determined by chemical analysis) is shown in the first column and the grade calculated by the BMDP programme is shown across the top row of the output.

The entries (elements) of the table indicate the number of occasions where the actual grade (row on entry) and the computed grade (column of entry) are recorded.

When classification is correct on all occasions, all samples (entries) fall along the major diagonal of the table from top left to bottom right. In this case there were seven (7) cases of grade A, all classified correctly into the computer entry. Similarly there were 10 cases of grade B, 12 of C, 13 of D and 8 of E.

In a more realistic case where the classification is less than perfect, entries appear at locations other than on the major diagonal.

EXAMPLE 2

|  |  |  | Computer Result | | | | |
| --- | --- | --- | --- | --- | --- | --- | --- |
|  |  |  | A | B | C | D | E |
| Actual | A | 71.4 | 5 | 2 | 0 | 0 | 0 |
| Grade | B | 70.0 | 2 | 7 | 1 | 0 | 0 |
|  | C | 83.3 | 1 | 1 | 10 | 0 | 0 |
|  | D | 92.3 | 0 | 0 | 0 | 12 | 1 |
|  | E | 100.0 | 0 | 0 | 0 | 0 | 8 |
|  |  | 84.0 |  |  |  |  |  |

In this case, the seven cases of Grade A, five have been correctly classified as A, and two incorrectly as grade B. The percentage correct is, $$\frac{5}{7} \times 100 = 71.4\%$$

Of the 10 cases of grade B, 7 are correct, 2 are misclassified as grade A, and one case (1) misclassified as grade C.

The overall percentage correct for this example (those along major diagonal=42) is then $$\%\text{correct} = \frac{\text{Number along major diagonal}}{\text{Total number}} \times 100 = \frac{42}{50} \times 100 = 84.0\%$$

The actual grade codes for the samples tested and their average chemical analysis are given in Table 4 of the Appendix.

As can be seen, the grades display a considerable range in carbon analysis, and include rim, semi-killed and fully killed steels (R=rim, CS,S,WS=Semi-killed, W,WK,XK=Fully Killed).

Table 5 shows the actual matrix obtained as a summary of the results of grade classification on steel rounds (5.5 mm-20 mm).

Another method BMDP uses to describe the results obtained from its statistical analysis is to generate a canonical variable plot. This graph is a two dimensional representation of the relative placement and separations between individual groups (grades). This graph is shown as FIG. 5.

It can be seen that in the far top left of the graph the lowest carbon steels are represented. As the carbon level increases the grades are represented by locations towards the top centre of the graph and finally towards the top right for high carbon grades.

Higher manganese steels WK22, XK1320, XK1340 are shown as a band extending to the right at a lower position on the graph. Spring steel grades XK5155, XK9261 are shown on the far right and far right bottom respectively indicating the relative ease of separation or classification which can be made for these grades, based on their magnetic properties.

At low frequencies (5, 10 hz) the current traverses the entire cross-section of a steel specimen inserted into the coils.

Figure 6:
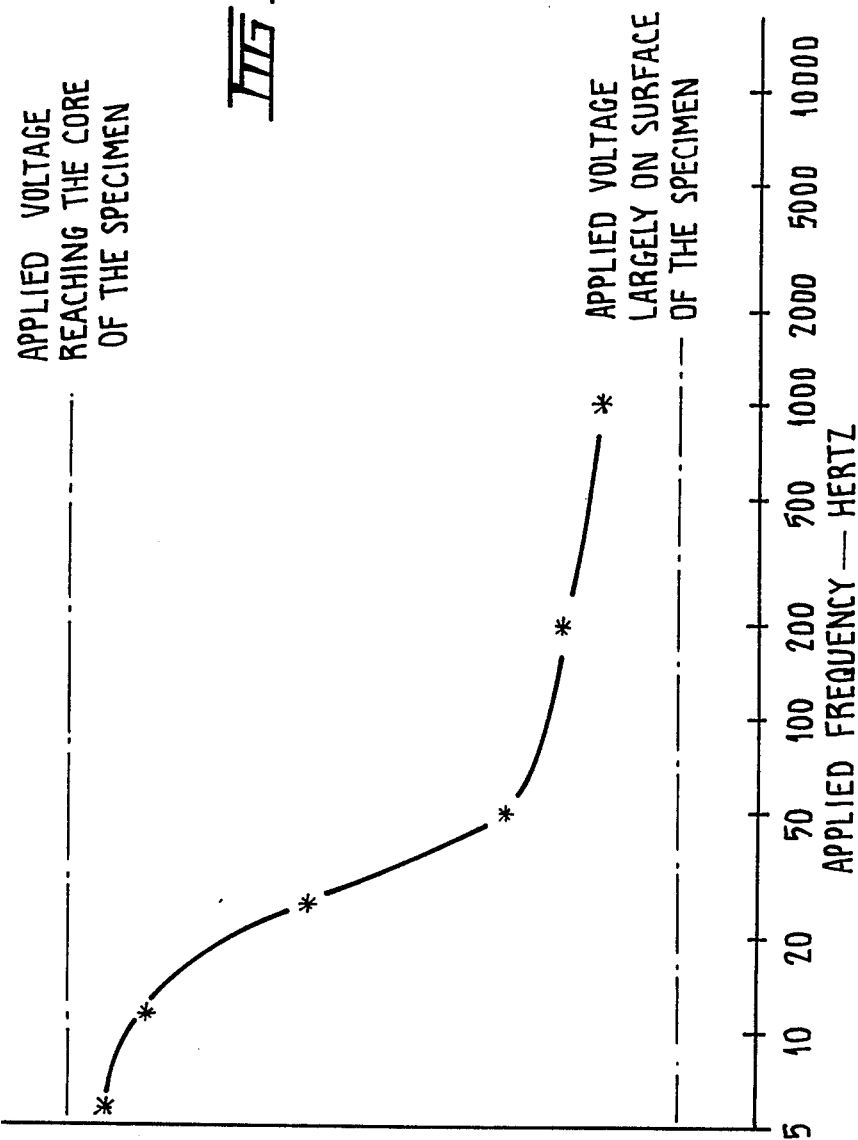
FIG. 6 is a diagram showing the skin effect for steel specimens at varying excitation frequencies.

The intensity of the current induced is therefore directly related to the cross-sectional area of the specimen (the volume or mass per unit length). At high frequencies (greater than 500 hertz) the current flow is confined almost entirely to the surface or skin of the conductor, as illustrated in FIG. 6.

There is a tendency for a varying electric current in a conductor to concentrate in the outer part, or "skin", rather than be distributed uniformly over the cross-section of the conductor. This "skin" effect arises from the increase of internal self inductance of the conductor with the depth below the surface of the conductor. In consequence, the magnitude of the effect increases with the rate of change (frequency) of the current, the diameter of the conductor and the magnetic permeability of the conductor material. By concentrating the current towards the outside of the conductor, skin effect increases the alternating current or skin resistance, and the energy dissipation within the conductor compared with when it is carrying a steady direct current.

Generally, the skin or penetration depth from the conductor's surface is given by:

$$d = 1/\sqrt{(\mu\mu_o fs)}, \quad \begin{array}{l} d \text{ being the depth at} \\ \text{which the current has} \\ \text{fallen to } 1/e \text{ of its} \\ \text{surface value.} \end{array}$$

$5\mu_o$ = permeability of free space
$\mu$ = permeability of the material
$f$ = the frequency of the applied current
$s$ = conductivity of the material All of the samples tested and computer classified were rounds (rods and rounds) between 5.5 and 20 mms in diameter. In order to investigate the behaviour of specimens with other sections, pieces of angles and flats of various dimensions were tested. The results of these tests are tabulated in Table 6.

The most significant differences relate to the ratio of surface area of the specimens compared with their mass (volume).

For rounds, the surface area per unit length is;
$S = \pi D$ where D is the diameter and the volume per unit length is;
$C = \pi D^2/4$
For a flat with thickness T and width W
$S = 2(T+W)$
$C = TW$
If we calculate an "aspect ratio" or shape factor which involves the square of the surface area divided by the volume, we obtain for a round.

$$\frac{S^2}{C} = \frac{\pi^2 D^2}{\pi D^2/4} = 4\pi$$

which is not dependent on the section of the steel specimen.

For a square we have:

$$\frac{S^2}{C} = \frac{2^2(T+W)^2}{TW} \text{ now } T = W$$

-continued $$\frac{S^2}{C} = \frac{4(2W)^2}{W^2} = 16$$

which is also independent of section size. For sections with large elongations (width/thickness ratio), the shape factors are much larger.

e.g. flat 10 mms × 100 mms $$\frac{S^2}{C} = \frac{(110 \times 2)^2}{1000} = \frac{(220)^2}{1000} = 48.4$$

It is possible to measure the relative volume (low frequency induction) to surface area (high frequency induction) of any specimen placed inside the coils by measuring the inductions induced at different applied current frequencies. In this manner it is possible to estimate the approximate section or shape being presented to the computer for grade analysis, thus avoiding the more obvious human entry errors of incorrect section input via the computer keyboard.

Figure 7:
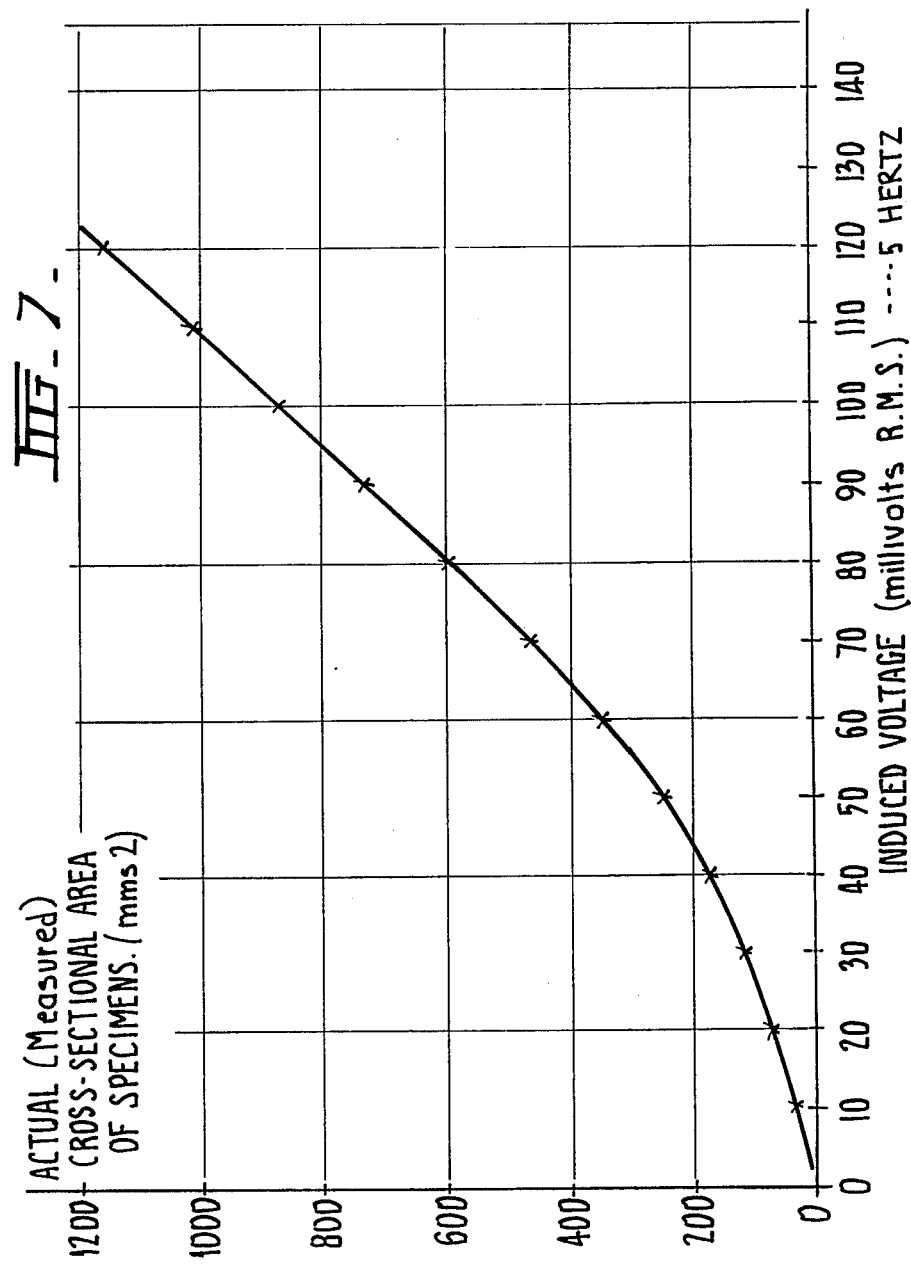
FIG. 7 illustrates the relationship between the induction and the cross-sectional area of the specimens.

For the particular coils used it was found that the induction did not increase linearly with cross sectional area (at low frequencies) but conformed to a curvilinear relationship as shown in FIG. 7. The induced voltage was almost but not quite linear with the measured surface area of the specimens as shown in FIG. 11.

Figure 8:
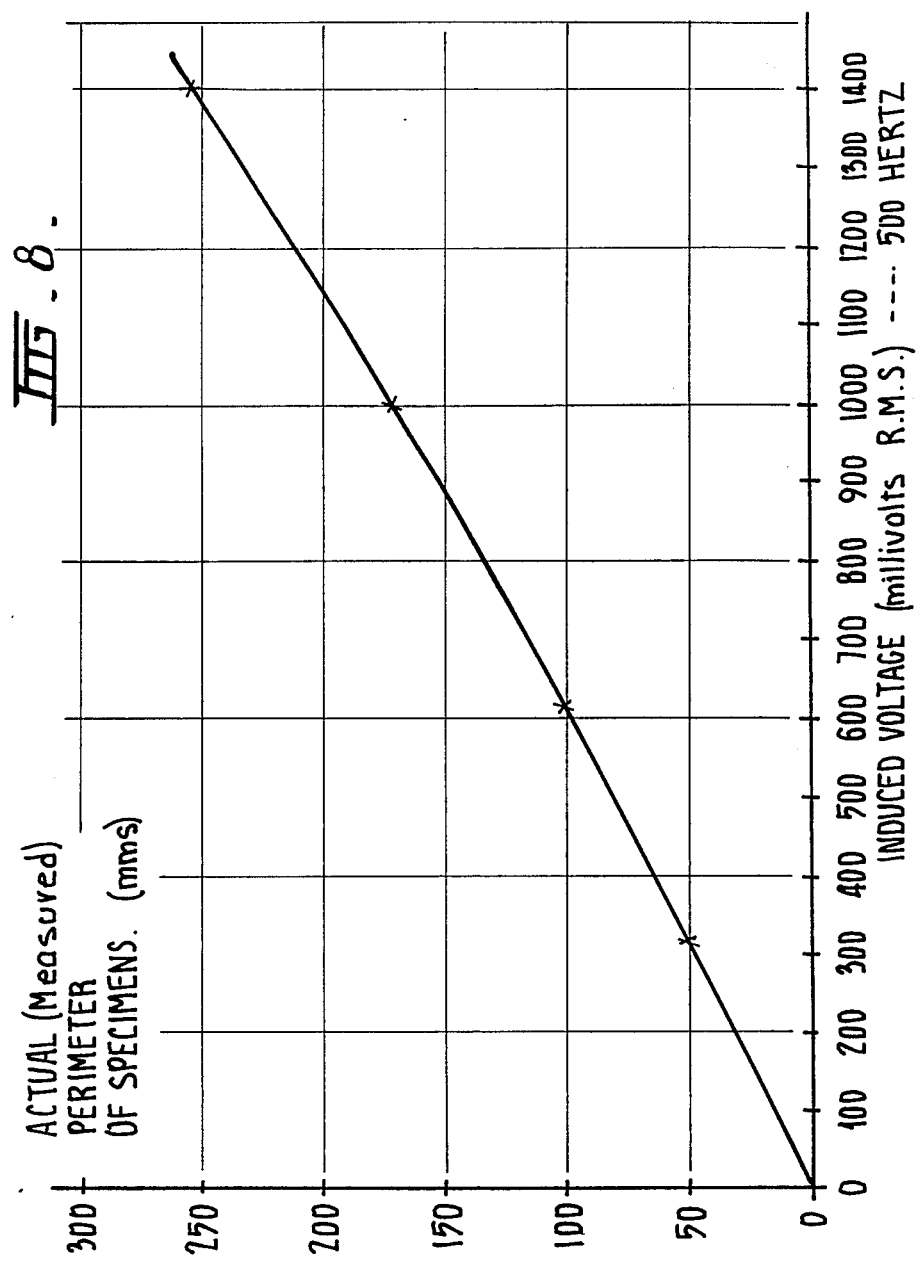
FIG. 8 illustrates the relationship between the induction and the measured surface area of the specimens.

From FIGS. 7 and 8 it is possible to estimate the shape factor of the specimen under test. For example the following values are measured for a specimen whose section has been INCORRECTLY typed in as a ROUND, prior to grade identification.

| I = | 5 hz | 500 hz |
|---|---|---|
| | 80.0 | 1150 millivolts |

Figure 9:
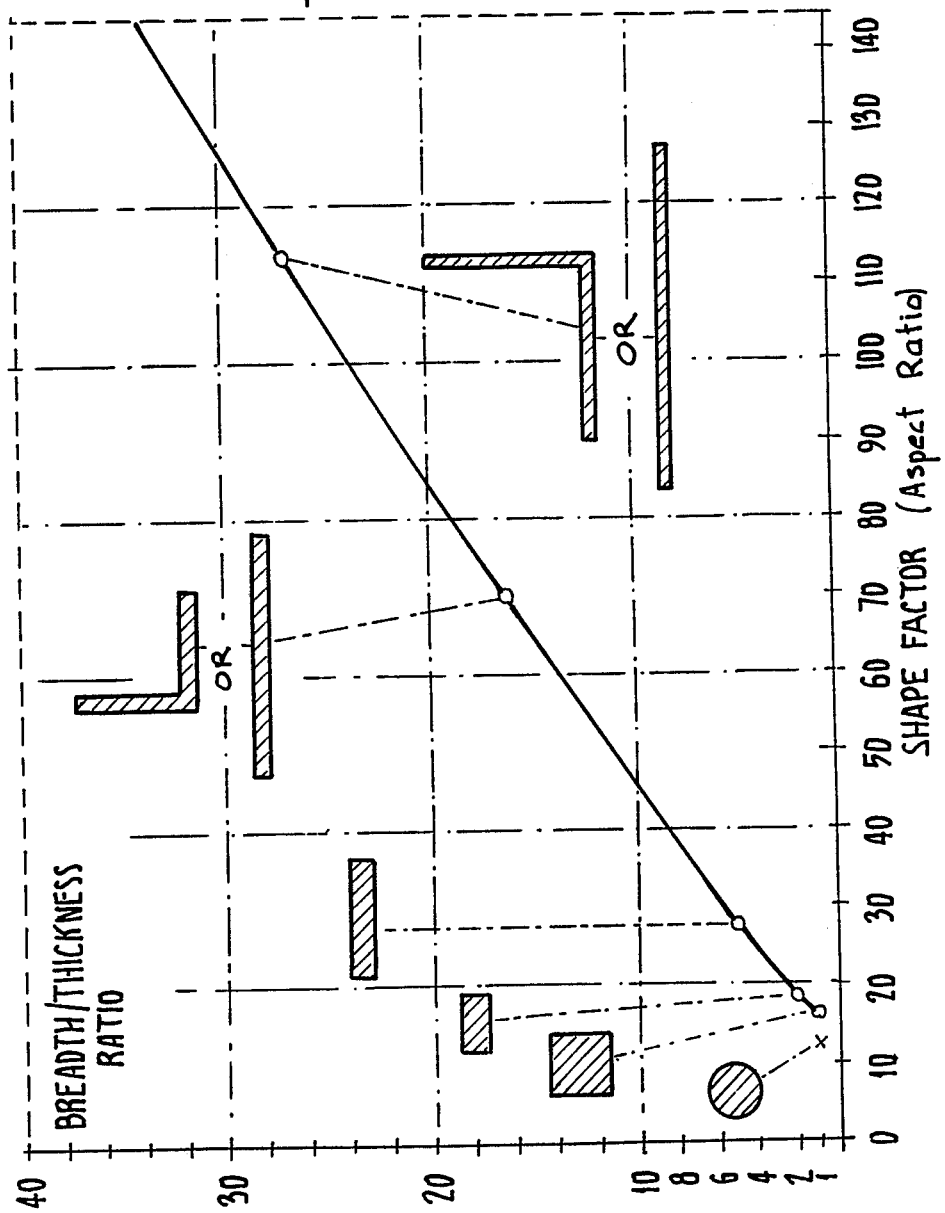
FIG. 9 is a plot of the shape factor of various specimens against a breadth/thickness ratio.

The computer would check the shape factor as follows:
80.0 = 590 mm² = C (FIG. 10), Mass (Volume)
1150 = 200 mm = S (FIG. 11), Surface Area $$\text{Now shape factor} = \frac{S^2}{C} = \frac{200 \times 200}{590} = 67.8$$

and therefore by referring to FIG. 9, with the above shape factor the breadth to thickness ratio is about 18 to 1, clearly indicating the sample is not a ROUND.

Since the volume is (approximately since it depends on grade) 590 mms² (cross section) the specimen is either a flat or angle (or channel) with a width/thickness ratio of 18/1 or 104×5.8 mms for a typical structural grade of steel.

Information can be gathered on other sections to form the basis for extending the method to all steel shapes produced at a particular steelworks where testing is to be conducted.

Problems relating to the surface decarburisation of steel occur quite frequently. In order to examine the possible use of the method of this invention for detecting the presence and extent of decarburisation, several steel specimens of a A grade prone to loss of carbon at the surface was examined.

Eight pieces of as rolled 20 mm round K1045 were taken and treated as follows:

(i) Samples 1 and 2 were left at 20 mms and used for comparison purposes.

(ii) The remaining samples were turned down to 18 mms in diameter to remove any decarburisation skin initially present on their surfaces.

(iii) Samples were heat treated individually, with slowly increasing oxidising conditions applied to the samples. (Details are given in Table 7 of the Appendix).

(iv) Metallographic examination was performed to define the extent of decarburisation of each specimen.

The ratio of the induction at 500 hertz (surface induction) to that obtained at 5 hertz (volumetric induction) is called RATIO 1. The correlation between the ratio and the reported decarburisation depth is demonstrated by FIG. 10. As can be seen the decarburised skin led to an increased induction on the surface of the specimen as expected.

Table 8 of the Appendix lists classification function coefficients actually determined for a wide range of steel grades and Tables 9, 10 and 11 show how these were used to classify three separate steel samples of unknown grade. The first sample was a 5.5 mm round section and as indicated in Table 9 each measured variable of the sample was multiplied by the appropriate coefficient and the result summed for all variables. This sum is calculated for all the possible grades and the grade whose sum is the maximum value is deemed to be the actual grade of the specimen. In Table 9 the highest value of 12072.895 was obtained from the coefficients for the grade WS1014 which was therefore determined as the appropriate grade.

Table 10 shows the results obtained from a second specimen which was 10 mm round. The maximum sum value of 12175.711 was obtained from the coefficients for the grade WS1014 and this specimen was also of that grade. In the case of Table 11, howevver, the maximum sum value of 13534.500 was obtained from the coefficients for the grade WK1082 which was therefore determined as the appropriate grade. The third specimen was 10 mm round and the first row of figures relating to section isn the same for Tables 10 and 11.

Industrial Applicability

From the above results it will be appropriate that the method of the present invention in which the absolute induction of a steel sample is measured at various applied frequencies is capable of classifying the specimen into a GRADE CODE which is the primary method of steel identification used both within steelworks and by customers. It allows a rapid means of steel identification and avoids most of the current limitations of the Forster instrumentation. The method can be applied to steel sections of various shapes and it can be usefully employed in the detection and measurement of surface decarburisation.

TABLE 1
APPENDIX

| BASE NO. | 1 LABEL | 2 SAMPLE | SECTION | 3 5 HZ | 4 10 HZ | 5 50 HZ | 6 500 HZ | 7 5K HZ | 8 10K HZ | 9 FREQN | 10 FREQC | 11 GRCOPE |
|---|---|---|---|---|---|---|---|---|---|---|---|---|
| 1 | 1142. | 5.5 MM | | 6.63500 | 13.6160 | 44.7930 | 144.561 | 270.485 | 335.107 | 43. | 31920. | K1010 |
| 2 | 2164. | 19.0 MM | | 15.5200 | 29.2180 | 83.4150 | 298.819 | 482.093 | 555.295 | 38. | 30010. | XK1340 |
| 3 | 2232. | 19.0 MM | | 25.0150 | 42.2410 | 112.386 | 371.897 | 621.764 | 741.966 | 32. | 29420. | K1030 |
| 4 | 2233. | 19.0 MM | | 25.1490 | 42.8230 | 111.507 | 358.146 | 624.476 | 740.260 | 32. | 29320. | K1030 |
| 5 | 2273. | 18.0 MM | | 18.3510 | 32.9410 | 90.9910 | 300.746 | 543.044 | 661.163 | 37. | 29625. | AS1442K5 |
| 6 | 2292. | 18.0 MM | | 14.2480 | 26.8750 | 82.4780 | 274.072 | 498.572 | 606.479 | 42. | 30010. | XK1340 |
| 7 | 2295. | 18.0 MM | | 13.7880 | 26.3860 | 82.5720 | 267.074 | 479.616 | 571.092 | 42. | 30000. | XK1340 |
| 8 | 2311. | 18.0 MM | | 16.9620 | 30.7640 | 80.5730 | 263.290 | 469.128 | 558.609 | 33. | 30050. | S1045 |
| 9 | 2341. | 18.0 MM | | 17.4190 | 31.4690 | 83.3230 | 274.456 | 470.116 | 548.983 | 34. | 30005. | S1045 |
| 10 | 2354. | 18.0 MM | | 17.1740 | 31.0350 | 83.2450 | 279.188 | 498.129 | 602.695 | 37. | 29955. | S1045 |
| 11 | 2355. | 18.0 MM | | 16.9550 | 30.3460 | 82.9630 | 279.214 | 497.612 | 598.412 | 37. | 30000. | S1045 |
| 12 | 2373. | 18.0 MM | | 17.3250 | 30.8150 | 81.6460 | 272.223 | 470.513 | 555.623 | 35. | 30035. | S1045 |
| 13 | 2393. | 16.0 MM | | 21.2700 | 37.6500 | 103.055 | 335.228 | 617.278 | 772.279 | 37. | 29435. | XK1320 |
| 14 | 2399. | 16.0 MM | | 21.2000 | 37.9320 | 104.253 | 345.534 | 616.160 | 798.786 | 38. | 29350. | XK1320 |
| 15 | 2419. | 16.0 MM | | 19.8880 | 35.4870 | 103.276 | 343.322 | 599.100 | 721.736 | 36. | 27420. | XK1320 |
| 16 | 2168. | 16.0 MM | | 14.0150 | 26.0830 | 72.9420 | 236.314 | 451.715 | 559.469 | 37. | 30255. | S1040 |
| 17 | 2472. | 14.0 MM | | 14.2870 | 26.5500 | 72.9440 | 236.051 | 432.820 | 519.508 | 35. | 30430. | S1040 |
| 18 | 2496. | 14.0 MM | | 18.9550 | 32.5570 | 84.0280 | 282.775 | 487.381 | 589.510 | 34.5000 | 30110. | CS1030 |
| 19 | 2502. | 14.0 MM | | 19.1110 | 33.2670 | 85.8530 | 283.662 | 521.190 | 643.404 | 34. | 30015. | CS1030 |
| 20 | 2516. | 14.0 MM | | 8.98800 | 17.6690 | 63.1030 | 204.915 | 379.734 | 459.693 | 50. | 30665. | XK1340 |
| 21 | 2533. | 14.0 MM | | 8.76400 | 17.2670 | 62.6810 | 218.435 | 378.029 | 465.716 | 51. | 30685. | XK1340 |
| 22 | 2547. | 14.0 MM | | 8.43500 | 16.6380 | 61.5070 | 199.358 | 374.019 | 451.671 | 53. | 30720. | XK1340 |
| 23 | 2557. | 14.0 MM | | 8.57400 | 16.9770 | 61.5680 | 198.546 | 372.135 | 450.029 | 50. | 30800. | XK1340 |
| 24 | 2558. | 14.0 MM | | 9.05100 | 18.1120 | 64.2870 | 207.637 | 392.228 | 470.851 | 53. | 30640. | XK1340 |
| 25 | 2569. | 14.0 MM | | 9.16600 | 18.0520 | 64.5230 | 208.339 | 384.617 | 462.547 | 53. | 30675. | XK1340 |
| 26 | 2576. | 14.0 MM | | 9.05700 | 17.9510 | 64.0310 | 207.265 | 383.769 | 460.887 | 54. | 30670. | XK1340 |
| 27 | 2599. | 15.0 MM | | 15.8670 | 28.9180 | 79.4430 | 265.133 | 497.096 | 615.762 | 35. | 30005. | S1040 |
| 28 | 2606. | 15.0 MM | | 14.4960 | 28.3010 | 79.6410 | 268.319 | 508.091 | 631.660 | 40. | 30025. | S1045 |
| 29 | 5131. | 5.5 MM | | 6.12600 | 12.2470 | 41.0400 | 132.814 | 251.328 | 308.932 | 46. | 31980. | WS1013 |
| 30 | 5133. | 5.5 MM | | 2.38800 | 5.17600 | 24.4320 | 92.1390 | 186.343 | 233.027 | 100.500 | 32520. | WS1033 |
| 31 | 5138. | 5.5 MM | | 0.690000 | 1.76200 | 10.5850 | 61.4860 | 131.878 | 168.813 | 447. | 33040. | WK1072 |
| 32 | 5139. | 5.5 MM | | 0.709200 | 1.88000 | 10.9250 | 60.8620 | 131.754 | 173.087 | 441. | 32905. | WK1072 |
| 33 | 5142. | 5.5 MM | | 6.66900 | 13.1530 | 44.7110 | 144.676 | 261.262 | 333.084 | 47. | 31850. | R1010 |
| 34 | 5143. | 5.5 MM | | 6.78300 | 12.8980 | 40.3970 | 128.015 | 237.839 | 289.636 | 37. | 32110. | WS1004 |
| 35 | 5144. | 5.5 MM | | 6.21500 | 12.5780 | 40.4100 | 131.505 | 236.649 | 285.255 | 41. | 32060. | WS1004 |
| 36 | 5178. | 5.5 MM | | 3.84000 | 8.11800 | 39.0060 | 149.427 | 300.891 | 381.830 | 113. | 31560. | WK22 |
| 37 | 5192. | 5.5 MM | | 3.81900 | 7.95700 | 38.4120 | 146.480 | 296.246 | 374.987 | 110. | 31520. | WK22 |
| 38 | 5201. | 5.5 MM | | 0.870000 | 2.22500 | 12.6140 | 66.5980 | 139.488 | 172.441 | 352. | 32965. | WK1057 |
| 39 | 5202. | 5.5 MM | | 1.23000 | 2.90700 | 15.7370 | 77.0860 | 162.433 | 215.259 | 275. | 32615. | WK1057 |
| 40 | 5905. | 10.0 MM | | 3.71300 | 7.71800 | 35.4060 | 113.246 | 236.121 | 287.556 | 90. | 31875. | WK1082 |
| 41 | 5970. | 8.0 MM | | 1.91000 | 4.25100 | 22.4640 | 90.4430 | 180.808 | 211.457 | 173. | 32380. | WK1077 |
| 42 | 5973. | 8.0 MM | | 10.8140 | 20.2100 | 55.1410 | 179.923 | 345.546 | 428.932 | 36. | 31115. | S1010 |
| 43 | 5995. | 8.0 MM | | 12.2800 | 22.7000 | 44.6250 | 195.212 | 354.840 | 431.725 | 34.5000 | 30965. | RL03 |
| 44 | 6103. | 6.5 MM | | 7.83000 | 15.1540 | 47.5160 | 156.151 | 300.929 | 403.835 | 43. | 31495. | XS1010 |

TABLE 1-continued

APPENDIX

| BASE NO. | 1 LABEL | 2 SAMPLE | 3 SECTION | 4 5 HZ | 5 10 HZ | 6 50 HZ | 7 500 HZ | 8 5K HZ | 9 10K HZ | 10 FREQN | 11 FREQC | GRCOPE |
|---|---|---|---|---|---|---|---|---|---|---|---|---|
| 45 | 6104. | 6.5 MM | 7.73600 | 14.9850 | 46.8560 | 155.827 | 295.102 | 363.338 | 43.5000 | 31555. | XS1010 | |
| 46 | 6105. | 6.5 MM | 8.35100 | 16.2020 | 50.1650 | 161.484 | 310.703 | 386.358 | 41. | 31410. | XS1010 | |
| 47 | 6106. | 6.5 MM | 7.60200 | 12.5340 | 45.8070 | 151.725 | 283.358 | 354.169 | 39. | 31565. | XS1010 | |
| 48 | 6107. | 6.5 MM | 7.25400 | 14.3560 | 46.0360 | 149.233 | 289.552 | 352.088 | 41. | 31510. | XS1010 | |
| 49 | 6108. | 6.5 MM | 7.23500 | 14.2660 | 47.0670 | 153.593 | 299.793 | 375.571 | 43.5000 | 31520. | XS1010 | |
| 50 | 6110. | 6.5 MM | 4.84900 | 10.0680 | 38.1480 | 131.695 | 262.946 | 316.910 | 55. | 31750. | SF2 | |
| 51 | 6111. | 6.5 MM | 5.24100 | 10.5870 | 39.2860 | 128.217 | 260.345 | 326.354 | 53. | 31745. | SF2 | |
| 52 | 6112. | 6.5 MM | 4.65100 | 9.38300 | 37.5730 | 129.133 | 261.514 | 325.994 | 61. | 31730. | SF2 | |
| 53 | 6113. | 6.5 MM | 5.43000 | 10.9840 | 42.4210 | 143.093 | 283.027 | 351.333 | 58. | 31670. | SF2 | |

TABLE 2

| | | | 5. Hz 0.687 | 50. Hz 2.464 | 500. Hz 26.593 | 5000. Hz 173.483 | 10. Hz 0.780 | 10000. Hz 289.858 | Natural | Coil |
|---|---|---|---|---|---|---|---|---|---|---|
| | Background level | | | | | | | | | |
| Case # | 1 | | | | | | | | | |
| Sample # | 5139.0 | Absolute | 1.394 | 13.384 | 87.420 | 305.103 | 2.659 | 462.942 | 441.0 | 32905.0 |
| Section | 5.5 mm | Relative | 0.707 | 10.920 | 60.827 | 131.620 | 1.879 | 173.084 | | |
| Analysis | 0.71% C | 0.72% Mn | 0.185% Si | 0.01% Cr | Grade Code # 1 | Grade name: WK1072 | | | | |
| Classification: WK1072 [96%] WK1082 [3%] | | | | | | | | | | |
| Case # | 2 | | | | | | | | | |
| Sample # | 5178.0 | Absolute | 4.525 | 41.465 | 175.985 | 474.240 | 8.897 | 671.685 | 113.0 | 31560.0 |
| Section | 5.5 mm | Relative | 3.838 | 39.001 | 149.393 | 300.757 | 8.118 | 381.827 | | |
| Analysis | 0.09% C | 1.32% Mn | 0.710% Si | 0.01% Cr | Grade code # 2 | Grade name: WK22 | | | | |
| Classification: WK22 [100%] SF2 [0%] | | | | | | | | | | |
| Case # | 3 | | | | | | | | | |
| Sample # | 5133.0 | Absolute | 3.073 | 26.891 | 118.697 | 359.692 | 5.955 | 522.882 | 100.5 | 32520.0 |
| Section | 5.5 mm | Relative | 2.386 | 24.427 | 92.104 | 186.209 | 5.175 | 233.024 | | |
| Analysis | 0.32% C | 0.94% Mn | 0.021% Si | 0.01% Cr | Grade code # 3 | Grade name: WS1033 | | | | |
| Classification: SF2 [100% ] CS1030 [0%] | | | | | | | | | | |
| Case # | 4 | | | | | | | | | |
| Sample # | 53614.0 | Absolute | 21.992 | 106.834 | 364.146 | 809.678 | 38.844 | 1045.274 | 35.0 | 29465.0 |
| Section | 16.0 mm | Relative | 21.305 | 104.370 | 337.553 | 636.195 | 38.065 | 755.416 | | |
| Analysis | 0.19% C | 1.52% Mn | 0.210% Si | 0.01% Cr | Grade code # 4 | Grade name: XK1320 | | | | |
| Classification: XK1320 [100%] SF2 [0%] | | | | | | | | | | |
| Case # | 5 | | | | | | | | | |
| Sample # | 5138.0 | Absolute | 1.375 | 13.044 | 88.044 | 305.227 | 2.541 | 458.668 | 447.0 | 33040.0 |
| Section | 5.5 mm | Relative | 0.688 | 10.580 | 61.451 | 131.744 | 1.761 | 168.810 | | |
| Analysis | 0.73% C | 0.70% Mn | 0.180% Si | 0.01% Cr | Grade code # 1 | Grade name: WK1072 | | | | |
| Classification: WK1072 [100%] WK1082 [0%] | | | | | | | | | | |
| Case # | 6 | | | | | | | | | |
| Sample # | 5192.0 | Absolute | 4.504 | 40.871 | 173.038 | 469.595 | 8.736 | 664.842 | 110.0 | 31520.0 |
| Section | 5.5 mm | Relative | 3.817 | 38.407 | 146.445 | 296.112 | 7.957 | 374.984 | | |
| Analysis | 0.10% C | 1.32% Mn | 0.780% Si | 0.01% Cr | Grade code # 2 | Grade name: WK22 | | | | |
| Classification: WK22 [100%] SF2 [0%] | | | | | | | | | | |

TABLE 3

| | | | 5. Hz 0.687 | 50. Hz 2.464 | 500. Hz 26.593 | 5000. Hz 173.483 | 10. Hz 0.780 | 10000. Hz 289.858 | Natural | Coil |
|---|---|---|---|---|---|---|---|---|---|---|
| | Background level | | | | | | | | | |
| Case # | 35 | | | | | | | | | |
| Sample # | 52118.0 | Absolute | 4.234 | 36.466 | 142.218 | 385.877 | 8.292 | 545.240 | 90.0 | 32005.0 |
| Section | 10.0 mm | Relative | 3.547 | 34.002 | 115.626 | 212.394 | 7.512 | 255.382 | | |
| Analysis | 0.85% C | 0.74% Mn | 0.190% Si | 0.01% Cr | Grade code # 15 | Grade name: WK1082 | | | | |
| Classification: WK1082 [100%] WK1072 [0%] | | | | | | | | | | |
| Case # | 36 | | | | | | | | | |
| Sample # | 66430.0 | Absolute | 10.272 | 58.571 | 212.709 | 528.837 | 19.125 | 737.551 | 36.0 | 30500.0 |
| Section | 10.0 mm | Relative | 9.585 | 56.107 | 186.117 | 355.354 | 18.345 | 447.693 | | |
| Analysis | 0.22% C | 0.75% Mn | 0.016% Si | 0.01% Cr | Grade code # 12 | Grade name: AS1302 | | | | |
| Classification: SF2 [98%] CS1030 [2%] | | | | | | | | | | |
| Case # | 37 | | | | | | | | | |
| Sample # | 53736.0 | Absolute | 17.927 | 87.686 | 308.810 | 716.578 | 31.955 | 1018.156 | 36.0 | 29950.0 |
| Section | 13.0 mm | Relative | 17.240 | 85.222 | 282.217 | 543.095 | 31.175 | 728.298 | | |
| Analysis | 0.23% C | 0.80% Mn | 0.035% Si | 0.01% Cr | Grade code # 16 | Grade name: SF2 | | | | |
| Classification: SF2 [90%] XK1320 [9%] | | | | | | | | | | |
| Case # | 38 | | | | | | | | | |
| Sample # | 53669.0 | Absolute | 5.402 | 45.118 | 167.027 | 415.232 | 10.572 | 600.079 | 79.5 | 31650.0 |
| Section | 13.0 mm | Relative | 4.715 | 42.654 | 140.434 | 241.749 | 9.792 | 310.221 | | |
| Analysis | 0.54% C | 0.85% Mn | 0.210% Si | 0.82% Cr | Grade code # 17 | Grade name: XK5155 | | | | |
| Classification: XK5155 [100%] WK1082 [0%] | | | | | | | | | | |
| Case # | 39 | | | | | | | | | |
| Sample # | 39030.0 | Absolute | 8.443 | 61.026 | 219.961 | 542.180 | 16.010 | 756.596 | 61.0 | 31000.0 |
| Section | 13.0 mm | Relative | 7.756 | 58.562 | 193.368 | 368.697 | 15.231 | 466.738 | | |
| Analysis | 0.40% C | 1.61% Mn | 0.260% Si | 0.02% Cr | Grade code # 18 | Grade name: XK1340 | | | | |
| Classification: XK1340 [100%] WK1082 [0%] | | | | | | | | | | |
| Case # | 40 | | | | | | | | | |
| Sample # | 53704.0 | Absolute | 8.438 | 75.332 | 302.391 | 727.534 | 16.586 | 1172.740 | 106.0 | 29800.0 |

TABLE 3-continued

|  | 5. Hz | 50. Hz | 500. Hz | 5000. Hz | 10. Hz | 10000. Hz | Natural | Coil |
|---|---|---|---|---|---|---|---|---|
| Background level | 0.687 | 2.464 | 26.593 | 173.483 | 0.780 | 289.858 |  |  |

Section 13.0 mm Relative 7.751 72.868 275.798 554.051 15.807 882.882
Analysis 0.58% C 0.83% Mn 2.150% Si 0.20% Cr Grade code # 19 Grade name: XK9261
Classification: XK9261 [100%] XK1340 [0%]
Case # 41
Sample # 398.0 Absolute 22.382 104.106 359.157 774.016 39.400 1076.582 34.5 29150.0
Section 16.0 mm Relative 21.695 101.642 332.565 600.533 38.621 786.724
Analysis 0.00% C 0.00% Mn 0.000% Si 0.00% Cr Grade code # 20 Grade name: AS1442
Classification: XK1320 [100%] SF2 [0%]

TABLE 4
CHEMICAL ANALYSIS OF GRADES EXAMINED (%)

| Grade Name | C | Mn | Si | Cr |
|---|---|---|---|---|
| N72 | .06 | .37 | .007 | .01 |
| R1010 | .10 | .45 | .007 | .01 |
| WK22 | .10 | 1.32 | .75 | .01 |
| WS1013 | .09 | .32 | .10 | .01 |
| WS1014 | .11 | .40 | .04 | .01 |
| SF2 | .22 | .79 | .03 | .01 |
| CS1030 | .27 | .76 | .03 | .01 |
| XK1320 | .20 | 1.50 | .22 | .01 |
| XK1340 | .39 | 1.60 | .24 | .01 |
| S1045 | .45 | .77 | .02 | .01 |
| XK5155 | .53 | .85 | .20 | .85 |
| XK9261 | .57 | .83 | 2.00 | .20 |
| WK1057 | .57 | .70 | .17 | .01 |
| WK1072 | .74 | .72 | .18 | .01 |
| WK1082 | .84 | .72 | .18 | .01 |

TABLE 5
CLASSIFICATION MATRIX

| GROUP | PERCENT CORRECT | N72 | R1010 | WK22 | WS1013 | WS1014 | SF2 | CS1030 | XK1320 | XK1340 | S1045 | XK5155 | XK9261 | WK1057 | WK1072 | WK1082 |
|---|---|---|---|---|---|---|---|---|---|---|---|---|---|---|---|---|
| N72 | 100.0 | 11 | 0 | 0 | 0 | 0 | 0 | 0 | 0 | 0 | 0 | 0 | 0 | 0 | 0 | 0 |
| R1010 | 80.0 | 0 | 4 | 0 | 1 | 0 | 0 | 0 | 0 | 0 | 0 | 0 | 0 | 0 | 0 | 0 |
| WK22 | 100.0 | 0 | 0 | 3 | 0 | 0 | 0 | 0 | 0 | 0 | 0 | 0 | 0 | 0 | 0 | 0 |
| WS1013 | 80.5 | 0 | 5 | 0 | 33 | 3 | 0 | 0 | 0 | 0 | 0 | 0 | 0 | 0 | 0 | 0 |
| WS1014 | 94.4 | 0 | 0 | 0 | 4 | 84 | 1 | 0 | 0 | 0 | 0 | 0 | 0 | 0 | 0 | 0 |
| SF2 | 93.3 | 0 | 0 | 0 | 0 | 0 | 14 | 0 | 1 | 0 | 0 | 0 | 0 | 0 | 0 | 0 |
| CS1030 | 100.0 | 0 | 0 | 0 | 0 | 0 | 0 | 3 | 0 | 0 | 0 | 0 | 0 | 0 | 0 | 0 |
| XK1320 | 100.0 | 0 | 0 | 0 | 0 | 0 | 0 | 0 | 6 | 0 | 0 | 0 | 0 | 0 | 0 | 0 |
| XK1340 | 92.3 | 0 | 0 | 0 | 0 | 0 | 0 | 0 | 0 | 12 | 0 | 0 | 0 | 1 | 0 | 0 |
| S1045 | 100.0 | 0 | 0 | 0 | 0 | 0 | 0 | 0 | 0 | 0 | 8 | 0 | 0 | 0 | 0 | 0 |
| XK5155 | 100.0 | 0 | 0 | 0 | 0 | 0 | 0 | 0 | 0 | 0 | 0 | 4 | 0 | 0 | 0 | 0 |
| XK9261 | 100.0 | 0 | 0 | 0 | 0 | 0 | 0 | 0 | 0 | 0 | 0 | 0 | 2 | 0 | 0 | 0 |
| WK1057 | 100.0 | 0 | 0 | 0 | 0 | 0 | 0 | 0 | 0 | 0 | 0 | 0 | 0 | 4 | 0 | 0 |
| WK1072 | 66.7 | 0 | 0 | 0 | 0 | 0 | 0 | 0 | 0 | 0 | 0 | 0 | 0 | 1 | 10 | 4 |
| WK1082 | 80.0 | 0 | 0 | 0 | 0 | 0 | 0 | 0 | 0 | 0 | 0 | 0 | 0 | 0 | 1 | 4 |
| TOTAL | 90.2 | 11 | 9 | 3 | 38 | 87 | 15 | 3 | 7 | 12 | 8 | 4 | 2 | 6 | 11 | 8 |

TABLE 6

| SAMPLE NO | SECTION | 5 | 10 | 50 | 100 | 500 | S/C mmg−1 | DIMENSIONS mms. | CROSS SECT sq. mms. | SURFACE mms. | S*S/C | O |
|---|---|---|---|---|---|---|---|---|---|---|---|---|
|  |  | Induction-Millivolts (at the indicated frequency) |  |  |  |  |  |  |  |  |  |  |
| 1 | ROUND | 8.3 | 14.4 | 57.0 | 79.0 | 108 | 0.73 | 5.5 | 23.76 | 17.28 | 12.57 | 1.0 |
| 2 | " | 12.8 | 22.0 | 72.0 | 95.0 | 145 | 0.62 | 6.5 | 33.18 | 20.42 | 12.57 | 1.0 |
| 3 | " | 20.2 | 33.2 | 93.0 | 125.0 | 188 | 0.50 | 8.0 | 50.26 | 25.13 | 12.57 | 1.0 |
| 4 | " | 29.8 | 45.4 | 116.0 | 155.0 | 255 | 0.40 | 10.0 | 78.54 | 31.42 | 12.57 | 1.0 |
| S1 | ANGLE | 39.1 | 67.0 | 272.5 | 415 | 625 | 0.64 | 3.3 × 25.8 × 25.8 | 170.0 | 109.6 | 70.66 | 5.6 |

TABLE 6-continued

| SAMPLE NO | SECTION | 5 | 10 | 50 | 100 | 500 | S/C mmg−1 | DIMENSIONS mms. | CROSS SECT sq. mms. | SURFACE mms. | S*S/C | O |
|---|---|---|---|---|---|---|---|---|---|---|---|---|
| | | Induction-Millivolts (at the indicated frequency) | | | | | | | | | | |
| S2 | " | 53.2 | 92.8 | 380.0 | 596 | 885 | 0.63 | 3.3 × 39.7 × 39.7 | 262.0 | 165.4 | 104.42 | 8.3 |
| S3 | " | 63.7 | 111.2 | 462.0 | 725 | 1135 | 0.65 | 3.2 × 50.1 × 51.3 | 324.5 | 209.2 | 134.87 | 10.7 |
| S4 | " | 82.2 | 135.7 | 570.0 | 837 | 1265 | 0.43 | 4.85 × 64.1 × 64.2 | 622.2 | 266.3 | 113.97 | 9.0 |
| S5 | " | 64.2 | 111.7 | 380.0 | 532 | 900 | 0.34 | 6.25 × 39.9 × 40.1 | 500.0 | 172.5 | 59.51 | 4.7 |
| S6 | " | 86.4 | 140.7 | 471.0 | 656 | 1145 | 0.33 | 6.55 × 44.0 × 44.0 | 576.4 | 189.1 | 62.04 | 4.9 |
| S7 | " | 130.7 | 195.2 | 628.0 | 909 | 1565 | 0.22 | 10.00 × 65.0 × 66.5 | 1315.0 | 283.0 | 60.90 | 4.8 |
| S8 | FLAT | 92.2 | 149.2 | 483.0 | 686 | 1175 | 0.26 | 8.3 × 86 | 717.9 | 189.6 | 50.07 | 3.9 |
| S9 | " | 72.7 | 116.2 | 325.0 | 452 | 765 | 0.24 | 10.1 × 50.6 | 511.1 | 121.4 | 28.84 | 2.2 |
| S10 | " | 47.7 | 76.2 | 212.0 | 298 | 495 | 0.25 | 12.0 × 23.8 | 285.6 | 71.6 | 17.95 | 1.4 |
| S11 | " | 24.2 | 36.2 | 104.0 | 137 | 262 | 0.39 | 10.2 × 10.2 | 104.0 | 40.8 | 16.00 | 1.4 |
| S12 | " | 58.7 | 77.7 | 209.0 | 285 | 445 | 0.23 | 12.0 × 32.5(S1040) | 390.0 | 89.0 | 20.31 | 1.4 |
| S13 | PIPE | 49.0 | 82.9 | 230.0 | 294 | 405 | 0.35 | 27.0(OD),20.5(ID) | 242.5 | 84.8 | 29.65 | 2. |

TABLE 7

DECARBURISATION TEST-K1045

| SAMPLE NO. | SECTION mms. | HEAT TREATMENT | FREQUENCIES IN HERTZ | | | | FREQ. RATIO 1 | FREQ. RATIO 2 | FREQ. RATIO 3 | DE-CARBURISATION DEPTH mms. |
|---|---|---|---|---|---|---|---|---|---|---|
| | | | 5 | 50 | 500 | 5000 | | | | |
| A | 20 | As rolled | 46.5 | 238 | 837 | 1460 | 18.0 | 31.4 | 5.12 | N.D. |
| B | 20 | As rolled | 50.0 | 245 | 840 | 1465 | 16.8 | 29.3 | 4.90 | N.D. |
| 1 | 18 | 20 mins @ 950* | 49.5 | 244 | 821 | 1375 | 16.6 | 27.8 | 4.93 | 0.07 |
| 2 | 18 | 30 min @ 950 | 42.5 | 209 | 701 | 1261 | 16.5 | 29.6 | 4.92 | 0.11 |
| 3 | 18 | 60 min @ 950 | 41.0 | 208 | 756 | 1425 | 18.4 | 34.8 | 5.07 | 0.15 |
| 4 | 18.2 | 120 min @ 950 | 37.0 | 206 | 767 | 1448 | 20.7 | 39.1 | 5.57 | 0.18 |
| 5 | 18.2 | 240 min @ 950 | 37.5 | 223 | 907 | 1578 | 24.2 | 42.1 | 5.95 | 0.25 |
| 6 | 18.2 | 120 min @ 1000 | 42.5 | 253 | 1045 | 1659 | 24.6 | 39.0 | 5.95 | 0.30–0.35 |
| K1030 (Comparison) sample | 18 | As rolled | 44.5 | 204 | 673 | 1161 | 15.1 | 26.1 | 4.58 | N.D. |

*Sample 1 was wrapped in steel sheet to prevent surface oxidation
Samples 1-6 were turned down to approx. 18 mms to remove any decarburisation present on the surface of the rounds prior to heat treatment
FREQ. RATIO 1 = Induction at 500 hertz/Induction at 5 hertz
FREQ. RATIO 2 = Induction at 5k hertz/Induction at 5 hertz
FREQ. RATIO 3 = Induction at 50 hertz/Induction at 5 hertz
The DECARBURISATION was determined by metallographic examination

TABLE 8

| COLUMN | 1 | Group = N72 | | | |
|---|---|---|---|---|---|
| ROW | 1 | Variable 2 | Name SECTION | Coeff = | 705.04028 |
| ROW | 2 | Variable 3 | Name 5 HZ | Coeff = | −42.02381 |
| ROW | 3 | Variable 5 | Name 50 HZ | Coeff = | 16.84021 |
| ROW | 4 | Variable 17 | Name RATIO5 | Coeff = | 85.67964 |
| ROW | 5 | Variable 18 | Name RATIO11 | Coeff = | −0.75230 |
| ROW | 6 | Variable 19 | Name ALPHA | Coeff = | 0.06502 |
| ROW | 7 | Variable 20 | Name AREA5 | Coeff = | 335.59445 |
| ROW | 8 | Variable 21 | Name AREA500 | Coeff = | −6.83658 |
| ROW | 9 | Variable 22 | Name AREACOIL | Coeff = | 0.55114 |
| | | | | Const = | −12284.69434 |
| COLUMN | 2 | Group = R1010 | | | |
| ROW | 1 | Variable 2 | Name SECTION | Coeff = | 704.40845 |
| ROW | 2 | Variable 3 | Name 5 HZ | Coeff = | −45.14893 |
| ROW | 3 | Variable 5 | Name 50 HZ | Coeff = | 17.92215 |
| ROW | 4 | Variable 17 | Name RATIO5 | Coeff = | 86.29301 |
| ROW | 5 | Variable 18 | Name RATIO11 | Coeff = | −0.74992 |
| ROW | 6 | Variable 19 | Name ALPHA | Coeff = | 0.06459 |
| ROW | 7 | Variable 20 | Name AREA5 | Coeff = | 333.01642 |
| ROW | 8 | Variable 21 | Name AREA500 | Coeff = | −6.24165 |
| ROW | 9 | Variable 22 | Name AREACOIL | Coeff = | 0.55183 |
| | | | | Const = | −12387.92676 |
| COLUMN | 3 | Group = WK22 | | | |
| ROW | 1 | Variable 2 | Name SECTION | Coeff = | 714.29883 |
| ROW | 2 | Variable 3 | Name 5 HZ | Coeff = | −48.86045 |
| ROW | 3 | Variable 5 | Name 50 HZ | Coeff = | 16.98532 |
| ROW | 4 | Variable 17 | Name RATIO5 | Coeff = | 91.16546 |
| ROW | 5 | Variable 18 | Name RATIO11 | Coeff = | −0.96404 |
| ROW | 6 | Variable 19 | Name ALPHA | Coeff = | 0.07379 |
| ROW | 7 | Variable 20 | Name AREA5 | Coeff = | 318.06665 |
| ROW | 8 | Variable 21 | Name AREA500 | Coeff = | −6.11734 |
| ROW | 9 | Variable 22 | Name AREACOIL | Coeff = | 0.55004 |
| | | | | Const = | −12431.23145 |
| COLUMN | 4 | Group = WS1013 | | | |
| ROW | 1 | Variable 2 | Name SECTION | Coeff = | 703.41846 |

TABLE 8-continued

| | | | | | |
|---|---|---|---|---|---|
| ROW | 2 | Variable 3 | Name 5 HZ | Coeff = | −43.57568 |
| ROW | 3 | Variable 5 | Name 50 HZ | Coeff = | 17.03631 |
| ROW | 4 | Variable 17 | Name RATIO5 | Coeff = | 85.70042 |
| ROW | 5 | Variable 18 | Name RATIO11 | Coeff = | −0.75417 |
| ROW | 6 | Variable 19 | Name ALPHA | Coeff = | 0.06459 |
| ROW | 7 | Variable 20 | Name AREA5 | Coeff = | 327.24362 |
| ROW | 8 | Variable 21 | Name AREA500 | Coeff = | −6.18792 |
| ROW | 9 | Variable 22 | Name AREACOIL | Coeff = | 0.54944 |
| | | | | Const = | −12240.80664 |
| COLUMN | 5 | Group = WS1014 | | | |
| ROW | 1 | Variable 2 | Name SECTION | Coeff = | 703.71759 |
| ROW | 2 | Variable 3 | Name 5 HZ | Coeff = | −42.13168 |
| ROW | 3 | Variable 5 | Name 50 HZ | Coeff = | 16.75370 |
| ROW | 4 | Variable 17 | Name RATIO5 | Coeff = | 85.34000 |
| ROW | 5 | Variable 18 | Name RATIO11 | Coeff = | −0.75325 |
| ROW | 6 | Variable 19 | Name ALPHA | Coeff = | 0.06436 |
| ROW | 7 | Variable 20 | Name AREA5 | Coeff = | 320.12674 |
| ROW | 8 | Variable 21 | Name AREA500 | Coeff = | −6.39298 |
| ROW | 9 | Variable 22 | Name AREACOIL | Coeff = | 0.55051 |
| | | | | Const = | −12204.54102 |
| COLUMN | 6 | Group = SF2 | | | |
| ROW | 1 | Variable 2 | Name SECTION | Coeff = | 706.80884 |
| ROW | 2 | Variable 3 | Name 5 HZ | Coeff = | −46.95062 |
| ROW | 3 | Variable 5 | Name 50 HZ | Coeff = | 17.51089 |
| ROW | 4 | Variable 17 | Name RATIO5 | Coeff = | 88.30956 |
| ROW | 5 | Variable 18 | Name RATIO11 | Coeff = | −0.84434 |
| ROW | 6 | Variable 19 | Name ALPHA | Coeff = | 0.06749 |
| ROW | 7 | Variable 20 | Name AREA5 | Coeff = | 313.34344 |
| ROW | 8 | Variable 21 | Name AREA500 | Coeff = | −6.94147 |
| ROW | 9 | Variable 22 | Name AREACOIL | Coeff = | 0.54927 |
| | | | | Const = | −12157.76074 |
| COLUMN | 7 | Group = CS1030 | | | |
| ROW | 1 | Variable 2 | Name SECTION | Coeff = | 717.46100 |
| ROW | 2 | Variable 3 | Name 5 HZ | Coeff = | −43.77097 |
| ROW | 3 | Variable 5 | Name 50 HZ | Coeff = | 16.30962 |
| ROW | 4 | Variable 17 | Name RATIO5 | Coeff = | 88.68691 |
| ROW | 5 | Variable 18 | Name RATIO11 | Coeff = | −0.82266 |
| ROW | 6 | Variable 19 | Name ALPHA | Coeff = | 0.06607 |
| ROW | 7 | Variable 20 | Name AREA5 | Coeff = | 315.32489 |
| ROW | 8 | Variable 21 | Name AREA500 | Coeff = | −6.95524 |
| ROW | 9 | Variable 22 | Name AREACOIL | Coeff = | 0.55391 |
| | | | | Const = | −12352.09766 |
| COLUMN | 8 | Group = XK1320 | | | |
| ROW | 1 | Variable 2 | Name SECTION | Coeff = | 703.40894 |
| ROW | 2 | Variable 3 | Name 5 HZ | Coeff = | −58.99757 |
| ROW | 3 | Variable 5 | Name 50 HZ | Coeff = | 22.40871 |
| ROW | 4 | Variable 17 | Name RATIO5 | Coeff = | 93.56011 |
| ROW | 5 | Variable 18 | Name RATIO11 | Coeff = | −0.93446 |
| ROW | 6 | Variable 19 | Name ALPHA | Coeff = | 0.07206 |
| ROW | 7 | Variable 20 | Name AREA5 | Coeff = | 328.51236 |
| ROW | 8 | Variable 21 | Name AREA500 | Coeff = | −8.56967 |
| ROW | 9 | Variable 22 | Name AREACOIL | Coeff = | 0.54806 |
| | | | | Const = | −12265.76660 |
| COLUMN | 9 | Group = XK1340 | | | |
| ROW | 1 | Variable 2 | Name SECTION | Coeff = | 761.18042 |
| ROW | 2 | Variable 3 | Name 5 HZ | Coeff = | −58.48672 |
| ROW | 3 | Variable 5 | Name 50 HZ | Coeff = | 18.67416 |
| ROW | 4 | Variable 17 | Name RATIO5 | Coeff = | 97.57011 |
| ROW | 5 | Variable 18 | Name RATIO11 | Coeff = | −0.98014 |
| ROW | 6 | Variable 19 | Name ALPHA | Coeff = | 0.07751 |
| ROW | 7 | Variable 20 | Name AREA5 | Coeff = | 337.80484 |
| ROW | 8 | Variable 21 | Name AREA500 | Coeff = | −9.02742 |
| ROW | 9 | Variable 22 | Name AREACOIL | Coeff = | 0.57412 |
| | | | | Const = | −13477.85547 |
| COLUMN | 10 | Group = S1045 | | | |
| ROW | 1 | Variable 2 | Name SECTION | Coeff = | 755.34595 |
| ROW | 2 | Variable 3 | Name 5 HZ | Coeff = | −47.96958 |
| ROW | 3 | Variable 5 | Name 50 HZ | Coeff = | 14.42558 |
| ROW | 4 | Variable 17 | Name RATIO5 | Coeff = | 92.71995 |
| ROW | 5 | Variable 18 | Name RATIO11 | Coeff = | −0.88787 |
| ROW | 6 | Variable 19 | Name ALPHA | Coeff = | 0.07254 |
| ROW | 7 | Variable 20 | Name AREA5 | Coeff = | 326.52554 |
| ROW | 8 | Variable 21 | Name AREA500 | Coeff = | −7.66458 |
| ROW | 9 | Variable 22 | Name AREACOIL | Coeff = | 0.56499 |
| | | | | Const = | −13004.06738 |

TABLE 8-continued

| COLUMN | 11 | Group = XK5155 | | | |
|---|---|---|---|---|---|
| ROW | 1 | Variable 2 | Name SECTION | Coeff = | 806.06689 |
| ROW | 2 | Variable 3 | Name 5 HZ | Coeff = | −57.57134 |
| ROW | 3 | Variable 5 | Name 50 HZ | Coeff = | 16.79425 |
| ROW | 4 | Variable 17 | Name RATIO5 | Coeff = | 101.28144 |
| ROW | 5 | Variable 18 | Name RATIO11 | Coeff = | −0.98835 |
| ROW | 6 | Variable 19 | Name ALPHA | Coeff = | 0.07777 |
| ROW | 7 | Variable 20 | Name AREA5 | Coeff = | 345.51135 |
| ROW | 8 | Variable 21 | Name AREA500 | Coeff = | −9.09016 |
| ROW | 9 | Variable 22 | Name AREACOIL | Coeff = | 0.60007 |
| | | | | Const = | −14723.12988 |
| COLUMN | 12 | Group = XK9261 | | | |
| ROW | 1 | Variable 2 | Name SECTION | Coeff = | 742.84131 |
| ROW | 2 | Variable 3 | Name 5 HZ | Coeff = | −83.52076 |
| ROW | 3 | Variable 5 | Name 50 HZ | Coeff = | 28.88023 |
| ROW | 4 | Variable 17 | Name RATIO5 | Coeff = | 103.05659 |
| ROW | 5 | Variable 18 | Name RATIO11 | Coeff = | −1.33720 |
| ROW | 6 | Variable 19 | Name ALPHA | Coeff = | 0.11708 |
| ROW | 7 | Variable 20 | Name AREA5 | Coeff = | 399.50494 |
| ROW | 8 | Variable 21 | Name AREA500 | Coeff = | −14.19436 |
| ROW | 9 | Variable 22 | Name AREACOIL | Coeff = | 0.57025 |
| | | | | Const = | −14100.03320 |
| COLUMN | 13 | Group = WK1057 | | | |
| ROW | 1 | Variable 2 | Name SECTION | Coeff = | 745.09485 |
| ROW | 2 | Variable 3 | Name 5 HZ | Coeff = | −47.03363 |
| ROW | 3 | Variable 5 | Name 50 HZ | Coeff = | 16.24667 |
| ROW | 4 | Variable 17 | Name RATIO5 | Coeff = | 98.74570 |
| ROW | 5 | Variable 18 | Name RATIO11 | Coeff = | −1.07716 |
| ROW | 6 | Variable 19 | Name ALPHA | Coeff = | 0.07543 |
| ROW | 7 | Variable 20 | Name AREA5 | Coeff = | 324.76114 |
| ROW | 8 | Variable 21 | Name AREA500 | Coeff = | −8.85161 |
| ROW | 9 | Variable 22 | Name AREACOIL | Coeff = | 0.56794 |
| | | | | Const = | −13087.95020 |
| COLUMN | 14 | Group = WK1072 | | | |
| ROW | 1 | Variable 2 | Name SECTION | Coeff = | 761.74701 |
| ROW | 2 | Variable 3 | Name 5 HZ | Coeff = | −50.54107 |
| ROW | 3 | Variable 5 | Name 50 HZ | Coeff = | 16.94999 |
| ROW | 4 | Variable 17 | Name RATIO5 | Coeff = | 99.63231 |
| ROW | 5 | Variable 18 | Name RATIO11 | Coeff = | −1.04633 |
| ROW | 6 | Variable 19 | Name ALPHA | Coeff = | 0.07642 |
| ROW | 7 | Variable 20 | Name AREA5 | Coeff = | 331.75217 |
| ROW | 8 | Variable 21 | Name AREA500 | Coeff = | −9.21887 |
| ROW | 9 | Variable 22 | Name AREACOIL | Coeff = | 0.57852 |
| | | | | Const = | −13573.81738 |
| COLUMN | 15 | Group = WS1082 | | | |
| ROW | 1 | Variable 2 | Name SECTION | Coeff = | 763.97028 |
| ROW | 2 | Variable 3 | Name 5 HZ | Coeff = | −51.22761 |
| ROW | 3 | Variable 5 | Name 50 HZ | Coeff = | 17.06170 |
| ROW | 4 | Variable 17 | Name RATIO5 | Coeff = | 97.81107 |
| ROW | 5 | Variable 18 | Name RATIO11 | Coeff = | −0.98401 |
| ROW | 6 | Variable 19 | Name ALPHA | Coeff = | 0.07397 |
| ROW | 7 | Variable 20 | Name AREA5 | Coeff = | 328.05502 |
| ROW | 8 | Variable 21 | Name AREA500 | Coeff = | −8.87672 |
| ROW | 9 | Variable 22 | Name AREACOIL | Coeff = | 0.58086 |
| | | | | Const = | −13626.97852 |

TABLE 9

| No | Variable | Value | N72 | R1010 | WK22 | WS1013 | WS1014 | SF2 | CS1030 |
|---|---|---|---|---|---|---|---|---|---|
| 2 | SECTION | 5.500 | 3877.722 | 3874.247 | 3928.644 | 6868.802 | 3870.447 | 3877.449 | 3946.035 |
| 3 | 5 HZ | 5.160 | −216.843 | −232.968 | −252.120 | −224.850 | −217.399 | −242.265 | −225.858 |
| 5 | 50 HZ | 37.918 | 638.547 | 679.572 | 644.049 | 645.983 | 635.267 | 663.978 | 618.428 |
| 17 | RATIO5 | 11.219 | 961.199 | 968.080 | 1022.742 | 961.432 | 957.389 | 990.703 | 994.936 |
| 18 | RATIO11 | 9.884 | −7.436 | −7.412 | −9.528 | −7.454 | −7.445 | −8.345 | −8.131 |
| 19 | ALPHA | 6529.901 | 424.574 | 421.766 | 481.841 | 421.766 | 420.264 | 440.703 | 431.431 |
| 20 | AREA5 | 5.160 | 1731.667 | 1718.365 | 1641.224 | 1688.577 | 1651.854 | 1616.852 | 1627.076 |
| 21 | AREA500 | 105.864 | −723.747 | −660.766 | −647.606 | −655.078 | −676.786 | −734.851 | −736.309 |
| 22 | AREACOIL | 32050.000 | 17664.037 | 17686.150 | 17628.781 | 17609.553 | 17643.846 | 17604.104 | 17752.816 |
| | Constant | | −12284.694 | −12387.927 | −12431.231 | −12240.807 | −12204.541 | −12157.761 | −12352.098 |
| | Equation Totals | | 12065.026 | 12059.106 | 12006.796 | 12067.924 | 12072.895 | 12060.567 | 12048.328 |

| No | Variable | Value | XK1320 | XK1340 | S1045 | XK5155 | XK9261 | WK1057 | WK1072 | WK1082 |
|---|---|---|---|---|---|---|---|---|---|---|
| 2 | SECTION | 5.500 | 3868.749 | 4186.492 | 4154.403 | 4433.368 | 4085.627 | 4098.021 | 4189.608 | 4201.836 |
| 3 | 5 HZ | 5.160 | −304.427 | −310.791 | −247.523 | −297.068 | −430.967 | −242.694 | −260.792 | −264.334 |
| 5 | 50 HZ | 37.918 | 849.693 | 708.087 | 546.989 | 636.804 | 1095.081 | 616.041 | 642.710 | 646.946 |
| 17 | RATIO5 | 11.219 | 1049.606 | 1094.593 | 1040.181 | 1136.228 | 1156.143 | 1107.781 | 1117.727 | 1097.296 |

TABLE 9-continued

| No | Variable | Value | | | | | | | | |
|----|----------|---------|----------|----------|----------|----------|----------|----------|----------|----------|
| 18 | RATIO11 | 9.884 | −9.236 | −9.687 | −8.775 | −9.769 | −13.217 | −10.646 | −10.342 | −9.726 |
| 19 | ALPHA | 6529.901 | 470.545 | 506.133 | 473.679 | 507.830 | 764.521 | 492.550 | 499.015 | 483.017 |
| 20 | AREA5 | 5.160 | 1695.124 | 1743.073 | 1684.872 | 1782.839 | 2061.446 | 1675.767 | 1711.841 | 1692.764 |
| 21 | AREA500 | 105.864 | −907.219 | −955.678 | −811.402 | −962.320 | −1502.671 | −937.066 | −975.946 | −939.724 |
| 22 | AREACOIL | 32050.000 | 17565.322 | 18400.545 | 18107.930 | 19232.244 | 18276.512 | 18202.477 | 18541.566 | 18616.564 |
| Constant | | | −12265.767 | −13477.855 | −13004.067 | −14723.130 | −14100.033 | −13087.950 | −13573.817 | −13626.979 |
| Equation Totals | | | 12012.392 | 11893.910 | 11936.286 | 11737.028 | 11392.441 | 11914.282 | 11881.571 | 11897.660 |

TABLE 10

| No | Variable | Value | N72 | R1010 | WK22 | WS1013 | WS1014 | SF2 | CS1030 |
|----|----------|-------|-----|-------|------|--------|--------|-----|--------|
| 2 | SECTION | 10.000 | 7050.403 | 7044.084 | 7142.988 | 7034.185 | 7037.176 | 7068.088 | 7174.610 |
| 3 | 5 HZ | 16.802 | −706.084 | −758.592 | −820.953 | −732.159 | −707.896 | −788.864 | −735.440 |
| 5 | 50 HZ | 73.032 | 1229.874 | 1308.890 | 1240.472 | 1244.196 | 1223.556 | 1278.855 | 1191.124 |
| 17 | RATIO5 | 8.399 | 719.661 | 724.813 | 765.739 | 719.836 | 716.809 | 741.751 | 744.921 |
| 18 | RATIO11 | 1.964 | −1.478 | −1.473 | −1.893 | −1.481 | −1.479 | −1.658 | −1.616 |
| 19 | ALPHA | 7837.768 | 509.612 | 506.241 | 578.349 | 506.241 | 504.439 | 528.971 | 517.841 |
| 20 | AREA5 | 4.874 | 1635.786 | 1623.220 | 1550.350 | 1595.082 | 1560.392 | 1527.328 | 1536.986 |
| 21 | AREA500 | 120.205 | −821.790 | −750.277 | −735.334 | −743.818 | −768.467 | −834.399 | −836.054 |
| 22 | AREACOIL | 26912.727 | 14832.681 | 14851.250 | 14803.076 | 14786.929 | 14815.725 | 14782.353 | 14907.229 |
| Constant | | | −12284.694 | −12387.927 | −12431.231 | −12240.807 | −12204.541 | −12157.761 | −12352.098 |
| Equation Totals | | | 12163.972 | 12160.231 | 12091.563 | 12168.203 | 12175.711 | 12144.665 | 12147.504 |

| No | Variable | Value | XK1320 | XK1340 | S1045 | XK5155 | XK9261 | WK1057 | WK1072 | WK1082 |
|----|----------|-------|--------|--------|-------|--------|--------|--------|--------|--------|
| 2 | SECTION | 10.000 | 7034.089 | 7611.804 | 7553.459 | 8060.669 | 7428.413 | 7450.949 | 7617.470 | 7639.703 |
| 3 | 5 HZ | 16.802 | −991.277 | −982.694 | −805.985 | −967.314 | −1403.316 | −790.259 | −849.191 | −860.726 |
| 5 | 50 HZ | 73.032 | 1636.553 | 1363.811 | 1053.529 | 1226.518 | 2109.181 | 1186.527 | 1237.892 | 1246.050 |
| 17 | RATIO5 | 8.399 | 785.853 | 819.535 | 778.796 | 850.708 | 865.618 | 829.409 | 836.856 | 821.559 |
| 18 | RATIO11 | 1.964 | −1.835 | −1.925 | −1.744 | −1.941 | −2.626 | −2.116 | −2.005 | −1.933 |
| 19 | ALPHA | 7837.768 | 564.789 | 607.505 | 568.552 | 609.543 | 917.646 | 591.203 | 598.962 | 579.760 |
| 20 | AREA5 | 4.874 | 1601.266 | 1646.560 | 1591.581 | 1684.124 | 1947.304 | 1582.981 | 1617.057 | 1599.037 |
| 21 | AREA500 | 120.205 | −1030.116 | −1085.140 | −921.320 | −1092.682 | −1706.231 | −1064.007 | −1108.153 | −1057.025 |
| 22 | AREACOIL | 26912.727 | 14749.789 | 15451.134 | 15205.421 | 16149.520 | 15346.981 | 15284.813 | 15569.551 | 15632.526 |
| Constant | | | −12265.767 | −13477.855 | −13004.067 | −14723.130 | −14100.033 | −13087.950 | −13573.817 | −13626.979 |
| Equation Totals | | | 12083.345 | 11952.736 | 12018.222 | 11796.015 | 11402.938 | 11981.552 | 11944.573 | 11961.973 |

TABLE 11

| No | Variable | Value | N72 | R1010 | WK22 | WS1013 | WS1014 | SF2 | CS1030 |
|----|----------|-------|-----|-------|------|--------|--------|-----|--------|
| 2 | SECTION | 10.000 | 7050.403 | 7044.084 | 7142.988 | 7034.185 | 7037.176 | 7068.088 | 7174.610 |
| 3 | 5 HZ | 3.763 | −158.136 | −169.895 | −183.862 | −163.975 | −158.542 | −176.675 | −164.710 |
| 5 | 50 HZ | 35.462 | 597.188 | 635.555 | 602.333 | 604.142 | 594.120 | 620.971 | 578.372 |
| 17 | RATIO5 | 15.409 | 1320.244 | 1329.696 | 1404.776 | 1320.564 | 1315.011 | 1360.769 | 1366.584 |
| 18 | RATIO11 | 22.323 | −16.793 | −16.740 | −21.520 | −16.835 | −16.815 | −18.848 | −18.364 |
| 19 | ALPHA | 8176.804 | 531.656 | 528.140 | 603.366 | 528.140 | 526.259 | 551.852 | 540.241 |
| 20 | AREA5 | 1.092 | 366.353 | 363.539 | 347.219 | 357.237 | 349.468 | 342.063 | 344.226 |
| 21 | AREA500 | 60.184 | −411.453 | −375.648 | −368.166 | −372.414 | −384.756 | −417.766 | −418.595 |
| 22 | AREACOIL | 29603.637 | 16315.749 | 16336.175 | 16283.185 | 16265.423 | 16297.098 | 16260.389 | 16397.750 |
| Constant | | | −12284.694 | −12387.927 | −12431.231 | −12240.807 | −12204.541 | −12157.761 | −12352.098 |
| Equation Totals | | | 13310.517 | 13286.979 | 13379.089 | 13315.660 | 13354.479 | 13433.083 | 13448.016 |

| No | Variable | Value | XK1320 | XK1340 | S1045 | XK5155 | XK9261 | WK1057 | WK1072 | WK1082 |
|----|----------|-------|--------|--------|-------|--------|--------|--------|--------|--------|
| 2 | SECTION | 10.000 | 7034.089 | 7611.804 | 7553.459 | 8060.669 | 7428.413 | 7450.949 | 7617.470 | 7639.703 |
| 3 | 5 HZ | 3.763 | −222.008 | −220.086 | −180.510 | −216.641 | −314.289 | −176.988 | −190.186 | −192.770 |
| 5 | 50 HZ | 35.462 | 794.658 | 662.223 | 511.560 | 595.558 | 1024.151 | 576.139 | 601.081 | 605.042 |
| 17 | RATIO5 | 15.409 | 1441.675 | 1503.465 | 1428.729 | 1560.654 | 1588.007 | 1521.580 | 1535.242 | 1507.178 |
| 18 | RATIO11 | 22.323 | −20.860 | −21.879 | −19.820 | −22.063 | −29.850 | −24.045 | −23.357 | −21.966 |
| 19 | ALPHA | 8176.804 | 589.220 | 633.784 | 593.145 | 635.910 | 957.340 | 616.776 | 624.871 | 604.838 |
| 20 | AREA5 | 1.092 | 358.622 | 368.766 | 356.451 | 377.179 | 436.121 | 354.527 | 362.159 | 358.123 |
| 21 | AREA500 | 60.184 | −515.758 | −543.307 | −461.286 | −547.083 | −854.274 | −532.726 | −554.829 | −534.237 |
| 22 | AREACOIL | 29603.637 | 16224.569 | 16996.039 | 16725.758 | 17764.254 | 16881.473 | 16813.090 | 17126.297 | 17195.568 |
| Constant | | | −12265.767 | −13477.855 | −13004.067 | −14723.130 | −14100.033 | −13087.950 | −13573.817 | −13626.979 |
| Equation Totals | | | 13418.442 | 13512.955 | 13503.425 | 13485.308 | 13017.059 | 13511.354 | 13524.931 | 13534.500 |

I claim:

1. Method of classifying a steel specimen, comprising:
   presenting a steel specimen to a coil means, said coil means receiving an excitation current and producing an electrical output dependent on an induction value of said specimen;
   applying an excitation current to said coil means at each of a plurality of excitation frequencies in series and determining a respective induction value of said specimen at each of these frequencies;
   deriving for each of a plurality of possible steel grades a separate determinant function, said separate determinant function being a sum of a series of products of attributes of said specimen comprising said induction values and predetermined weighted coefficients reflecting the degree to which the respective attributes are effective to discriminate that possible steel grade from the others;
   producing a series of differing discriminant functions correlative with the differing possible steel grades and comprised of differing sets of weighted coefficients applied to the same values of said attributes of said specimens; and determining which of the differing discriminate functions has a maximum numerical value as a measure of which of the known grades most closely matches that of the specimen.

2. A method as claimed in claim 1, wherein said coefficients are predetermined by measuring the values of said attributes in a set of steel samples of all the possible grades.

3. A method as claimed in claim 1, wherein the critical frequencies at which the output induced in the secondary windings is 180° of phase with the excitation current are also determined and said attributes also comprise said critical frequencies.

4. A method as claimed in claim 1, wherein the coil means comprises a primary winding for receiving the excitation current and a secondary winding for producing an induced output, the primary and secondary windings being generally co-axial, the specimen being positioned so as to extend into both windings and contribute to an inductive coupling between the primary and secondary windings.

5. A method of classifying a steel specimen, comprising:
   presenting a steel specimen to coil means, said coil means receiving an excitation current and producing an electrical output dependent on an induction value of said specimen;
   applying an excitation current to said coil means at each of a plurality of excitation frequencies in series and determining a respective induction value of said specimen at each of those frequencies;
   determining critical frequencies at which the electrical output of said coil means at 180° out of phase with the excitation current; and
   deriving for each of a plurality of possible steel grades a separate discriminant function which is the sum of a series of products of attributes of said specimen comprising said induction values and said critical frequencies and predetermined weighted coefficients reflecting the degree to which the respective attributes are effective to discriminate that possible steel grade from the others;
   producing a series of differing discriminate functions correlating with differing possible steel grades and comprised of sets of weighted coefficients applied to the same values of said attributes of the specimen; and
   determining which of the differing discriminant functions has a maximum numerical value as a measure of which of the known grades most closely matches that of the specimen, wherein said coefficients are predetermined by measuring the value of said attributes in a set of steel samples of all the possible grades.

6. A method as claimed in claim 5, wherein said coil means comprises a primary winding for receiving the excitation current and a secondary winding for producing an induced output, the primary and secondary windings being generally coaxial and said specimen being positioned so as to extend into both windings and contribute to an inductuve coupling between them.

7. Apparatus for classifying steel specimens, comprising:
   coil means for receiving an excitation current and for producing an electrical output dependent on an induction value of a steel specimen presented thereto;
   excitation means for applying an excitation current to said coil means at each of a plurality of excitation frequencies in series to induce an output indicative of a respective induction value of said specimen at each of those frequencies; and
   signal processing means for receiving the electrical output indicative of the induction values of said frequencies, for deriving for each of a plurality of possible steel grades a separate discriminant function which is a sum of a series of products of attributes of the specimen, said attributes comprising said induction values and predetermined weighted coefficients reflecting the degree to which the respective attributes are effective to discriminate that possible steel grade from the others for producing a series of differing discriminate functions correlative with the differing possible steel grades and comprised of differing sets of weighted coefficients applied to the same values of said attributes of the specimen and for determining which of the differing discriminant functions has a maximum numerical value as a measure of which of the known grades most closely matches that of the specimen.

8. Apparatus as claimed in claim 7, wherein said attributes also comprise critical frequencies at which the induced output is 180° out of phase with the excitation current.

9. Apparatus as claimed in claim 7, wherein said coil means comprises a primary winding for receiving the excitation current and a secondary winding for producing an induced output, said primary and secondary windings being generally coaxial and arranged so that a specimen to be classified may be extended into both windings.

10. Apparatus for classifying steel specimens, comprising:
   coil means for receiving an excitation current and for producing an electrical output dependent on an induction value of a specimen presented thereto;
   excitation means for applying an excitation current to said coil means at each of a plurality of excitation frequencies in series to induce an output indicative of a respective induction value of the specimen at each of those frequencies and also to determine critical frequencies at which the output is 180° out of phase with the excitation current; and
   signal processing means for deriving for each of a plurality of possible steel grades a separate discriminant function which is the sum of a series of products of attributes of the specimen comprising said induction vales and said critical frequencies and predetermine weighted coefficients reflecting the degree to which the respective attributes are effective to discriminate that possible steel grade from the others for producing a series of differing discriminate functions correlative with the differing possible steel grades and comprised of differing sets of weighted coefficients applied to the same values of said attributes of the specimen and for determining which of the differing discriminant functions has a maximum numerical value as a measure of which of the known grades most closely matches that of the specimen, wherein the signal processing means is able to determine and store values of said coefficients for each of the possible steel grades on presentation to the apparatus of a set of steel samples of all the possible steel grades.

* * * * *